(12) United States Patent (10) Patent No.: US 9,142,117 B2
Muhsin et al. (45) Date of Patent: Sep. 22, 2015

(54) SYSTEMS AND METHODS FOR STORING, ANALYZING, RETRIEVING AND DISPLAYING STREAMING MEDICAL DATA

(71) Applicant: Masimo Corporation, Irvine, CA (US)

(72) Inventors: Bilal Muhsin, San Clemente, CA (US); Anand Sampath, Corona, CA (US); Travis Gruber, Rancho Santa Margarita, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 13/675,996

(22) Filed: Nov. 13, 2012

(65) Prior Publication Data

US 2013/0162433 A1 Jun. 27, 2013

Related U.S. Application Data

(63) Continuation of application No. 12/904,925, filed on Oct. 14, 2010, now Pat. No. 8,310,336, which is a continuation-in-part of application No. 12/249,806, filed on Oct. 10, 2008, now Pat. No. 8,274,360.

(60) Provisional application No. 60/979,531, filed on Oct. 12, 2007.

(51) Int. Cl.
*G08B 23/00* (2006.01)
*G08B 25/00* (2006.01)
*G06F 17/30* (2006.01)
(Continued)

(52) U.S. Cl.
CPC ........ *G08B 25/008* (2013.01); *G06F 17/30516* (2013.01); *G06F 19/322* (2013.01); *A61B 5/746* (2013.01); *G06F 19/327* (2013.01)

(58) Field of Classification Search
CPC ............ G08B 25/008; G06F 19/30516; G06F 19/322
USPC ...................................... 340/573.1
See application file for complete search history.

(56) References Cited

U.S. PATENT DOCUMENTS

| 3,646,606 A | 2/1972 | Buxton et al. |
| 4,051,522 A | 9/1977 | Healy et al. |

(Continued)

FOREIGN PATENT DOCUMENTS

| EP | 1443480 | 8/2004 |
| EP | 1576925 A | 9/2005 |

(Continued)

OTHER PUBLICATIONS

Decision to Refuse European Patent Application issued in European Application No. 08837990.4 on Apr. 10, 2012, European Application No. 08837990.4 is related to the present application.

(Continued)

*Primary Examiner* — Naomi Small
(74) *Attorney, Agent, or Firm* — Knobbe Martens Olson & Bear LLP

(57) ABSTRACT

A method of storing streaming physiological information obtained from a medical patient in a multi-patient monitoring environment includes receiving identification information, retrieving parameter descriptors, creating a round-robin database file, receiving a data stream, and using a predetermined data rate to map the data stream to locations in the round-robin database file.

7 Claims, 14 Drawing Sheets

(51) Int. Cl.
    *G06F 19/00* (2011.01)
    *A61B 5/00* (2006.01)

(56) References Cited

U.S. PATENT DOCUMENTS

| | | | |
|---|---|---|---|
| 4,216,462 A | 8/1980 | McGrath et al. | |
| 4,237,344 A | 12/1980 | Moore | |
| 4,356,475 A | 10/1982 | Neumann et al. | |
| 4,674,085 A | 6/1987 | Aranguren et al. | |
| 4,838,275 A | 6/1989 | Lee | |
| 4,852,570 A | 8/1989 | Levine | |
| 4,887,260 A | 12/1989 | Carden et al. | |
| 4,916,444 A | 4/1990 | King | |
| 4,920,339 A | 4/1990 | Friend et al. | |
| 4,960,128 A | 10/1990 | Gordon et al. | |
| 4,964,408 A | 10/1990 | Hink et al. | |
| 5,038,800 A | 8/1991 | Oba | |
| 5,041,187 A | 8/1991 | Hink et al. | |
| 5,061,916 A | 10/1991 | French et al. | |
| 5,069,213 A | 12/1991 | Polczynski | |
| 5,163,438 A | 11/1992 | Gordon et al. | |
| 5,278,627 A | 1/1994 | Aoyagi | |
| 5,296,688 A | 3/1994 | Hamilton et al. | |
| 5,319,355 A | 6/1994 | Russek | |
| 5,319,363 A | 6/1994 | Welch et al. | |
| D348,463 S | 7/1994 | Scheid et al. | |
| 5,331,549 A | 7/1994 | Crawford, Jr. | |
| 5,337,744 A | 8/1994 | Branigan | |
| 5,341,805 A | 8/1994 | Stavridi et al. | |
| 5,348,008 A | 9/1994 | Bornn et al. | |
| D353,195 S | 12/1994 | Savage et al. | |
| D353,196 S | 12/1994 | Savage et al. | |
| 5,375,604 A | 12/1994 | Kelly et al. | |
| 5,377,676 A | 1/1995 | Vari et al. | |
| 5,416,695 A | 5/1995 | Stutman et al. | |
| D359,546 S | 6/1995 | Savage et al. | |
| 5,431,170 A | 7/1995 | Mathews | |
| 5,434,611 A | 7/1995 | Tamura | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,462,051 A | 10/1995 | Oka et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,544,649 A | 8/1996 | David et al. | |
| 5,553,609 A | 9/1996 | Chen et al. | |
| 5,558,638 A | 9/1996 | Evers et al. | |
| 5,561,275 A | 10/1996 | Savage et al. | |
| 5,562,002 A | 10/1996 | Lalin | |
| D375,792 S | 11/1996 | Hillman et al. | |
| 5,576,952 A | 11/1996 | Stutman et al. | |
| 5,579,001 A | 11/1996 | Dempsey et al. | |
| 5,579,775 A | 12/1996 | Dempsey et al. | |
| 5,590,649 A | 1/1997 | Caro et al. | |
| 5,602,924 A | 2/1997 | Durand et al. | |
| 5,619,991 A | 4/1997 | Sloane | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,682,803 A | 11/1997 | Boianjiu | |
| 5,685,299 A | 11/1997 | Diab et al. | |
| 5,687,734 A | 11/1997 | Dempsey et al. | |
| 5,694,940 A | 12/1997 | Unger et al. | |
| D390,666 S | 2/1998 | Lagerlof | |
| D392,639 S | 3/1998 | Tamura | |
| 5,724,580 A | 3/1998 | Levin et al. | |
| D393,830 S | 4/1998 | Tobler et al. | |
| 5,743,262 A | 4/1998 | Lepper, Jr. et al. | |
| 5,748,103 A | 5/1998 | Flach et al. | |
| 5,752,917 A | 5/1998 | Fuchs | |
| 5,758,079 A | 5/1998 | Ludwig et al. | |
| 5,758,644 A | 6/1998 | Diab et al. | |
| 5,760,910 A | 6/1998 | Lepper, Jr. et al. | |
| 5,767,791 A | 6/1998 | Stoop et al. | |
| 5,769,785 A | 6/1998 | Diab et al. | |
| 5,772,585 A | 6/1998 | Lavin et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,822,544 A | 10/1998 | Chaco et al. | |
| 5,823,950 A | 10/1998 | Diab et al. | |
| 5,830,131 A | 11/1998 | Caro et al. | |
| 5,833,618 A | 11/1998 | Caro et al. | |
| D402,805 S | 12/1998 | Nagano et al. | |
| 5,855,550 A | 1/1999 | Lai et al. | |
| 5,860,919 A | 1/1999 | Kiani-Azarbayjany et al. | |
| 5,871,451 A | 2/1999 | Unger et al. | |
| 5,877,675 A * | 3/1999 | Rebstock et al. | 340/286.07 |
| 5,890,929 A | 4/1999 | Mills et al. | |
| D409,195 S | 5/1999 | Halstead et al. | |
| 5,904,654 A | 5/1999 | Wohltmann et al. | |
| 5,919,134 A | 7/1999 | Diab | |
| 5,924,074 A | 7/1999 | Evans | |
| 5,934,925 A | 8/1999 | Tobler et al. | |
| 5,940,182 A | 8/1999 | Lepper, Jr. et al. | |
| 5,942,986 A | 8/1999 | Shabot et al. | |
| 5,960,431 A | 9/1999 | Choy | |
| D414,870 S | 10/1999 | Saltzstein et al. | |
| 5,987,519 A | 11/1999 | Peifer et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,024,699 A | 2/2000 | Surwit et al. | |
| 6,027,452 A | 2/2000 | Flaherty et al. | |
| 6,036,642 A | 3/2000 | Diab et al. | |
| D423,504 S | 4/2000 | Nishii et al. | |
| 6,045,509 A | 4/2000 | Caro et al. | |
| 6,057,758 A | 5/2000 | Dempsey et al. | |
| 6,067,462 A | 5/2000 | Diab et al. | |
| 6,081,735 A | 6/2000 | Diab et al. | |
| 6,088,607 A | 7/2000 | Diab et al. | |
| 6,093,146 A | 7/2000 | Filangeri | |
| 6,101,478 A | 8/2000 | Brown | |
| 6,110,522 A | 8/2000 | Lepper, Jr. et al. | |
| 6,112,226 A | 8/2000 | Weaver et al. | |
| 6,124,597 A | 9/2000 | Shehada et al. | |
| 6,128,521 A | 10/2000 | Marro et al. | |
| 6,129,675 A | 10/2000 | Jay | |
| 6,139,494 A | 10/2000 | Cairnes | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,168,563 B1 | 1/2001 | Brown | |
| 6,171,237 B1 | 1/2001 | Avitall et al. | |
| 6,184,521 B1 | 2/2001 | Coffin et al. | |
| 6,206,830 B1 | 3/2001 | Diab et al. | |
| 6,221,012 B1 | 4/2001 | Maschke et al. | |
| 6,229,856 B1 | 5/2001 | Diab et al. | |
| 6,230,142 B1 | 5/2001 | Benigno et al. | |
| 6,232,609 B1 | 5/2001 | Snyder et al. | |
| 6,236,872 B1 | 5/2001 | Diab et al. | |
| 6,241,661 B1 * | 6/2001 | Schluess et al. | 600/300 |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| D450,679 S | 11/2001 | Soh | |
| 6,312,378 B1 | 11/2001 | Bardy | |
| 6,317,627 B1 | 11/2001 | Ennen et al. | |

(56) References Cited

U.S. PATENT DOCUMENTS

| | | | |
|---|---|---|---|
| 6,321,100 | B1 | 11/2001 | Parker |
| 6,322,502 | B1 | 11/2001 | Schoenberg et al. |
| D452,012 | S | 12/2001 | Phillips |
| 6,325,761 | B1 | 12/2001 | Jay |
| 6,329,139 | B1 | 12/2001 | Nova et al. |
| 6,334,065 | B1 | 12/2001 | Al-Ali et al. |
| 6,338,039 | B1 | 1/2002 | Lonski et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,364,834 | B1 | 4/2002 | Reuss et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,380,853 | B1 | 4/2002 | Long et al. |
| 6,385,589 | B1 | 5/2002 | Trusheim et al. |
| 6,388,240 | B2 | 5/2002 | Schulz et al. |
| 6,397,091 | B2 | 5/2002 | Diab et al. |
| 6,406,426 | B1 | 6/2002 | Reuss et al. |
| 6,424,249 | B1 | 7/2002 | Houvener |
| 6,430,437 | B1 | 8/2002 | Marro |
| 6,430,525 | B1 | 8/2002 | Weber et al. |
| 6,440,067 | B1 | 8/2002 | DeLuca et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,535,132 | B2 | 3/2003 | Waters et al. |
| 6,541,756 | B2 | 4/2003 | Schulz et al. |
| 6,542,764 | B1 | 4/2003 | Al-Ali et al. |
| 6,544,173 | B2 | 4/2003 | West et al. |
| 6,544,174 | B2 | 4/2003 | West et al. |
| 6,551,243 | B2 | 4/2003 | Bocionek et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,678,703 | B2 | 1/2004 | Rothschild et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,749,566 | B2 | 6/2004 | Russ |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,782,093 | B2 | 8/2004 | Uckun |
| 6,784,797 | B2 | 8/2004 | Smith et al. |
| 6,792,300 | B1 | 9/2004 | Diab et al. |
| 6,804,656 | B1 | 10/2004 | Rosenfeld |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,928,370 | B2 | 8/2005 | Anuzis et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,028,182 | B1 | 4/2006 | Killcommons |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,916 | B2 | 5/2006 | Tenerz et al. |
| 7,044,918 | B2 | 5/2006 | Diab |
| 7,062,251 | B2 | 6/2006 | Birkett et al. |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| D539,265 | S | 3/2007 | Tompkins et al. |
| 7,186,966 | B2 | 3/2007 | Al-Ali |
| 7,190,261 | B2 | 3/2007 | Al-Ali |
| 7,215,984 | B2 | 5/2007 | Diab et al. |
| 7,215,986 | B2 | 5/2007 | Diab et al. |
| 7,221,971 | B2 | 5/2007 | Diab et al. |
| 7,225,006 | B2 | 5/2007 | Al-Ali et al. |
| 7,225,007 | B2 | 5/2007 | Al-Ali et al. |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,431 | B2 | 8/2007 | Al-Ali et al. |
| 7,254,433 | B2 | 8/2007 | Diab et al. |
| 7,254,434 | B2 | 8/2007 | Schulz et al. |
| 7,256,429 | B2 | 8/2007 | Schurman et al. |
| 7,256,708 | B2 | 8/2007 | Rosenfeld |
| 7,272,425 | B2 | 9/2007 | Al-Ali |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| D554,616 | S | 11/2007 | Pierce |
| 7,292,883 | B2 | 11/2007 | De Felice et al. |
| 7,295,866 | B2 | 11/2007 | Al-Ali |
| 7,307,543 | B2 | 12/2007 | Rosenfeld |
| 7,315,825 | B2 | 1/2008 | Rosenfeld |
| 7,321,862 | B2 | 1/2008 | Rosenfeld |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |

(56) References Cited

U.S. PATENT DOCUMENTS

| | | | |
|---|---|---|---|
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,382,247 B2 | 6/2008 | Welch et al. |
| 7,383,070 B2 | 6/2008 | Diab et al. |
| 7,395,216 B2 | 7/2008 | Rosenfeld |
| 7,411,509 B2 | 8/2008 | Rosenfeld |
| 7,415,297 B2 | 8/2008 | Al-Ali et al. |
| 7,421,367 B2 | 9/2008 | Nye |
| 7,427,920 B2 | 9/2008 | Martin et al. |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,570,152 B2 | 8/2009 | Smith et al. |
| 7,596,398 B2 | 9/2009 | Al-Ali et al. |
| D603,836 S | 11/2009 | Hibbard et al. |
| 7,618,375 B2 | 11/2009 | Flaherty |
| D606,659 S | 12/2009 | Kiani et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| D614,305 S | 4/2010 | Al-Ali et al. |
| 7,706,896 B2 | 4/2010 | Music et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,778,851 B2 | 8/2010 | Schoenberg |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,831,450 B2 | 11/2010 | Schoenberg |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,933,642 B2 | 4/2011 | Istvan et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 7,991,625 B2 | 8/2011 | Rosenfeld |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,086,708 B2 * | 12/2011 | Breitgand et al. ............ 709/223 |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| D665,504 S | 8/2012 | Arimitsu |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | Sampath et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,326,649 B2 | 12/2012 | Rosenfeld |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,358,214 B2 | 1/2013 | Amigo |
| 8,359,080 B2 | 1/2013 | Diab et al. |

(56) References Cited

U.S. PATENT DOCUMENTS

| | | | |
|---|---|---|---|
| 8,364,223 B2 | 1/2013 | Al-Ali et al. |
| 8,364,226 B2 | 1/2013 | Diab et al. |
| D676,136 S | 2/2013 | Arimitsu |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,620,678 B2 | 12/2013 | Gotlib et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | Macneish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 2001/0040512 A1 | 11/2001 | Hines et al. |
| 2001/0046366 A1 | 11/2001 | Susskind |
| 2002/0013518 A1 | 1/2002 | West et al. |
| 2002/0042723 A1 | 4/2002 | Rice et al. |
| 2002/0167699 A1 | 11/2002 | Verplaetse et al. |
| 2002/0177758 A1 | 11/2002 | Schoenberg et al. |
| 2002/0198473 A1 | 12/2002 | Kumar et al. |
| 2003/0002653 A1 | 1/2003 | Uckun |
| 2003/0052787 A1 | 3/2003 | Zerhusen et al. |
| 2003/0058838 A1 | 3/2003 | Wengrovitz |
| 2003/0063010 A1* | 4/2003 | Smith et al. ............... 340/686.1 |
| 2004/0001101 A1 | 1/2004 | Trajkovic et al. |
| 2004/0002637 A1 | 1/2004 | Huang et al. |
| 2004/0102683 A1 | 5/2004 | Khanuja et al. |
| 2004/0127774 A1 | 7/2004 | Moore et al. |
| 2004/0133087 A1 | 7/2004 | Ali et al. |
| 2004/0148308 A1 | 7/2004 | Rajan et al. |
| 2004/0167804 A1 | 8/2004 | Simpson et al. |
| 2004/0172222 A1 | 9/2004 | Simpson et al. |
| 2004/0172301 A1 | 9/2004 | Mihai et al. |
| 2005/0004953 A1 | 1/2005 | Kurase |
| 2005/0055242 A1 | 3/2005 | Bello et al. |
| 2005/0065851 A1 | 3/2005 | Aronoff et al. |
| 2005/0125256 A1 | 6/2005 | Schoenberg et al. |
| 2005/0165519 A1 | 7/2005 | Ariyur et al. |
| 2005/0179553 A1* | 8/2005 | Lederer ........................ 340/506 |
| 2005/0206518 A1 | 9/2005 | Welch et al. |
| 2005/0231374 A1 | 10/2005 | Diem et al. |
| 2005/0232421 A1 | 10/2005 | Simons et al. |
| 2005/0242946 A1* | 11/2005 | Hubbard et al. ......... 340/539.12 |
| 2005/0251792 A1* | 11/2005 | Smith ........................ 717/131 |
| 2006/0080140 A1 | 4/2006 | Buttner et al. |
| 2006/0129713 A1 | 6/2006 | Xie |
| 2006/0135858 A1 | 6/2006 | Nidd et al. |
| 2006/0149597 A1 | 7/2006 | Powell et al. |
| 2006/0224326 A1 | 10/2006 | St. Ores et al. |
| 2006/0238333 A1 | 10/2006 | Welch et al. |
| 2006/0253042 A1 | 11/2006 | Stahmann et al. |

(56) References Cited

U.S. PATENT DOCUMENTS

| | | | |
|---|---|---|---|
| 2006/0253301 A1* | 11/2006 | Simms et al. | 705/2 |
| 2006/0288095 A1 | 12/2006 | Torok et al. | |
| 2006/0293571 A1 | 12/2006 | Bao et al. | |
| 2006/0294092 A1* | 12/2006 | Giang et al. | 707/5 |
| 2007/0073555 A1* | 3/2007 | Buist | 705/2 |
| 2007/0075965 A1 | 4/2007 | Huppi et al. | |
| 2007/0106126 A1* | 5/2007 | Mannheimer et al. | 600/300 |
| 2007/0109098 A1 | 5/2007 | Siemon et al. | |
| 2007/0129983 A1* | 6/2007 | Scherpbier et al. | 705/8 |
| 2007/0136102 A1* | 6/2007 | Rodgers | 705/3 |
| 2007/0180140 A1 | 8/2007 | Welch et al. | |
| 2007/0213599 A1* | 9/2007 | Siejko et al. | 600/300 |
| 2007/0239377 A1 | 10/2007 | Reiner | |
| 2007/0266389 A1 | 11/2007 | Ganguly et al. | |
| 2007/0273504 A1 | 11/2007 | Tran | |
| 2007/0279211 A1 | 12/2007 | Fenske et al. | |
| 2008/0004499 A1 | 1/2008 | Davis | |
| 2008/0059556 A1 | 3/2008 | Greenspan et al. | |
| 2008/0088414 A1 | 4/2008 | Suga et al. | |
| 2008/0157980 A1* | 7/2008 | Sachanandani et al. | 340/573.1 |
| 2008/0174551 A1 | 7/2008 | Ishibashi | |
| 2008/0194918 A1 | 8/2008 | Kulik et al. | |
| 2008/0262360 A1* | 10/2008 | Dalal et al. | 600/484 |
| 2009/0051545 A1 | 2/2009 | Koblasz | |
| 2009/0091458 A1 | 4/2009 | Deutsch | |
| 2009/0119330 A1 | 5/2009 | Sampath et al. | |
| 2009/0160541 A1 | 6/2009 | Liu et al. | |
| 2009/0184823 A1 | 7/2009 | Tessier | |
| 2009/0224907 A1 | 9/2009 | Sinha et al. | |
| 2009/0247984 A1 | 10/2009 | Lamego et al. | |
| 2009/0275844 A1 | 11/2009 | Al-Ali | |
| 2009/0299157 A1 | 12/2009 | Telfort et al. | |
| 2010/0004518 A1 | 1/2010 | Vo et al. | |
| 2010/0030040 A1 | 2/2010 | Poeze et al. | |
| 2010/0069725 A1 | 3/2010 | Al-Ali | |
| 2010/0234718 A1 | 9/2010 | Sampath et al. | |
| 2010/0235782 A1 | 9/2010 | Powell et al. | |
| 2010/0261979 A1 | 10/2010 | Kiani | |
| 2010/0274100 A1 | 10/2010 | Behar et al. | |
| 2010/0286488 A1 | 11/2010 | Cohen et al. | |
| 2010/0317936 A1 | 12/2010 | Al-Ali et al. | |
| 2011/0001605 A1 | 1/2011 | Kiani et al. | |
| 2011/0082711 A1 | 4/2011 | Poeze et al. | |
| 2011/0105854 A1 | 5/2011 | Kiani et al. | |
| 2011/0172967 A1 | 7/2011 | Al-Ali et al. | |
| 2011/0208015 A1 | 8/2011 | Welch et al. | |
| 2011/0209915 A1 | 9/2011 | Telfort et al. | |
| 2011/0213212 A1 | 9/2011 | Al-Ali | |
| 2011/0230733 A1 | 9/2011 | Al-Ali | |
| 2011/0237911 A1 | 9/2011 | Lamego et al. | |
| 2012/0059267 A1 | 3/2012 | Lamego et al. | |
| 2012/0116175 A1 | 5/2012 | Al-Ali et al. | |
| 2012/0179006 A1 | 7/2012 | Jansen et al. | |
| 2012/0209082 A1 | 8/2012 | Al-Ali | |
| 2012/0209084 A1 | 8/2012 | Olsen et al. | |
| 2012/0227739 A1 | 9/2012 | Kiani | |
| 2012/0265039 A1 | 10/2012 | Kiani | |
| 2012/0283524 A1 | 11/2012 | Kiani et al. | |
| 2012/0284053 A1 | 11/2012 | Rosenfeld | |
| 2012/0286955 A1 | 11/2012 | Welch et al. | |
| 2012/0296178 A1 | 11/2012 | Lamego et al. | |
| 2012/0302894 A1 | 11/2012 | Diab et al. | |
| 2012/0319816 A1 | 12/2012 | Al-Ali | |
| 2012/0330112 A1 | 12/2012 | Lamego et al. | |
| 2013/0023775 A1 | 1/2013 | Lamego et al. | |
| 2013/0041591 A1 | 2/2013 | Lamego | |
| 2013/0045685 A1 | 2/2013 | Kiani | |
| 2013/0046204 A1 | 2/2013 | Lamego et al. | |
| 2013/0060108 A1 | 3/2013 | Schurman et al. | |
| 2013/0060147 A1 | 3/2013 | Welch et al. | |
| 2013/0079610 A1 | 3/2013 | Al-Ali | |
| 2013/0096405 A1 | 4/2013 | Garfio | |
| 2013/0096936 A1 | 4/2013 | Sampath et al. | |
| 2013/0109935 A1 | 5/2013 | Al-Ali et al. | |
| 2013/0120142 A1 | 5/2013 | Wildman et al. | |
| 2013/0162433 A1 | 6/2013 | Muhsin et al. | |
| 2013/0178749 A1 | 7/2013 | Lamego | |
| 2013/0190581 A1 | 7/2013 | Al-Ali et al. | |
| 2013/0197328 A1 | 8/2013 | Diab et al. | |
| 2013/0211214 A1 | 8/2013 | Olsen | |
| 2013/0243021 A1 | 9/2013 | Siskavich | |
| 2013/0253334 A1 | 9/2013 | Al-Ali et al. | |
| 2013/0274571 A1 | 10/2013 | Diab et al. | |
| 2013/0296672 A1 | 11/2013 | O'Neil et al. | |
| 2013/0317327 A1 | 11/2013 | Al-Ali et al. | |
| 2013/0317370 A1 | 11/2013 | Dalvi et al. | |
| 2013/0324808 A1 | 12/2013 | Al-Ali et al. | |
| 2013/0324817 A1 | 12/2013 | Diab | |
| 2013/0331670 A1 | 12/2013 | Kiani | |
| 2013/0338461 A1 | 12/2013 | Lamego et al. | |
| 2014/0012100 A1 | 1/2014 | Al-Ali et al. | |
| 2014/0025306 A1 | 1/2014 | Weber et al. | |
| 2014/0031650 A1 | 1/2014 | Weber at al. | |
| 2014/0034353 A1 | 2/2014 | Al-Ali et al. | |
| 2014/0046674 A1 | 2/2014 | Rosenfeld | |
| 2014/0051952 A1 | 2/2014 | Reichgott et al. | |
| 2014/0051953 A1 | 2/2014 | Lamego et al. | |
| 2014/0051954 A1 | 2/2014 | Al-Ali et al. | |
| 2014/0058230 A1 | 2/2014 | Abdul-Hafiz et al. | |
| 2014/0066783 A1 | 3/2014 | Kiani et al. | |
| 2014/0073167 A1 | 3/2014 | Al-Ali et al. | |
| 2014/0077956 A1 | 3/2014 | Sampath et al. | |
| 2014/0081097 A1 | 3/2014 | Al-Ali et al. | |
| 2014/0081100 A1 | 3/2014 | Muhsin et al. | |
| 2014/0081175 A1 | 3/2014 | Telfort | |
| 2014/0094667 A1 | 4/2014 | Schurman et al. | |
| 2014/0100434 A1 | 4/2014 | Diab et al. | |
| 2014/0114199 A1 | 4/2014 | Lamego et al. | |
| 2014/0120564 A1 | 5/2014 | Workman et al. | |
| 2014/0121482 A1 | 5/2014 | Merritt et al. | |
| 2014/0121483 A1 | 5/2014 | Kiani | |
| 2014/0125495 A1 | 5/2014 | Al-Ali | |
| 2014/0127137 A1 | 5/2014 | Bellott et al. | |
| 2014/0128696 A1 | 5/2014 | Al-Ali | |
| 2014/0128699 A1 | 5/2014 | Al-Ali et al. | |
| 2014/0129702 A1 | 5/2014 | Lamego et al. | |
| 2014/0135588 A1 | 5/2014 | Al-Ali et al. | |
| 2014/0142399 A1 | 5/2014 | Al-Ali et al. | |
| 2014/0142401 A1 | 5/2014 | Al-Ali et al. | |
| 2014/0142402 A1 | 5/2014 | Al-Ali et al. | |
| 2014/0155712 A1 | 6/2014 | Lamego et al. | |
| 2014/0163344 A1 | 6/2014 | Al-Ali | |
| 2014/0163402 A1 | 6/2014 | Lamego et al. | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0194709 A1 | 7/2014 | Al-Ali et al. | |
| 2014/0194711 A1 | 7/2014 | Al-Ali | |
| 2014/0194766 A1 | 7/2014 | Al-Ali et al. | |
| 2014/0200420 A1 | 7/2014 | Al-Ali | |
| 2014/0200422 A1 | 7/2014 | Weber et al. | |
| 2014/0206963 A1 | 7/2014 | Al-Ali | |
| 2014/0213864 A1 | 7/2014 | Abdul-Hafiz et al. | |
| 2014/0243627 A1 | 8/2014 | Diab et al. | |
| 2014/0266790 A1 | 9/2014 | Al-Ali et al. | |
| 2014/0275808 A1 | 9/2014 | Poeze et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0275881 A1 | 9/2014 | Lamego et al. | |
| 2014/0288400 A1 | 9/2014 | Diab et al. | |
| 2014/0296664 A1 | 10/2014 | Bruinsma et al. | |
| 2014/0303520 A1 | 10/2014 | Telfort et al. | |
| 2014/0309506 A1 | 10/2014 | Lamego et al. | |
| 2014/0309559 A1 | 10/2014 | Telfort et al. | |
| 2014/0316228 A1 | 10/2014 | Blank et al. | |
| 2014/0323825 A1 | 10/2014 | Al-Ali et al. | |
| 2014/0330092 A1 | 11/2014 | Al-Ali et al. | |
| 2014/0330098 A1 | 11/2014 | Merritt et al. | |
| 2014/0330099 A1 | 11/2014 | Al-Ali et al. | |
| 2014/0333440 A1 | 11/2014 | Kiani | |
| 2014/0336481 A1 | 11/2014 | Shakespeare et al. | |
| 2014/0343436 A1 | 11/2014 | Kiani | |

(56) References Cited

U.S. PATENT DOCUMENTS

FOREIGN PATENT DOCUMENTS

| WO | WO 98/29790 | 7/1998 |
|---|---|---|
| WO | WO 99/13766 | 3/1999 |
| WO | WO 00/40143 A | 7/2000 |
| WO | WO 2002-067122 A | 8/2002 |
| WO | WO 2007/065015 A2 | 6/2007 |
| WO | WO 2009/049254 A2 | 4/2009 |

OTHER PUBLICATIONS

Emergin "General Overview," http://www.emergin.com/technology/default.html, downloaded and printed from the Internet on Dec. 1, 2006 in 2 pages.
EPO Communication Pursuant to Article 94(3) EPC in European Application No. 08837990.4 dated Dec. 27, 2010, European Application No. 08837990.4 is related to the present application.
Ho Hyun Kang et al., "Wired/Wireless Integrated Medical Information Prototype System Using Web Service." Enterprise Networking and Computing in Healthcare Industry, 2005. Healthcom 2005. Proceedings of 7th International Workshop on Busan, South Korea Jun. 23-25, 2005, Piscataway, NJ, USA, pp. 41-44. ISBN: 0-7803-8940-9.
International Search Report and Written Opinion for International Application No. PCT/US2006/046295, Dec. 17, 2007.
International Search Report for application No. PCT/US2008/079643 dated Jan. 11, 2010.
Lopez-Casado C. et al, Network architecture for global biomedical monitoring service, Engineering in Medicine and Biology Society, Sep. 1, 2005, pp. 2433-2436, Piscataway, NJ, USA.
Lubrin, E. et al., "An Architecture for Wearable, Wireless, Smart Biosensors: The MoteCare Prototype," Proceedings of the International Conference on Networking, International Conference on Systems, and International Conference on Mobile Communications and Learning Technologies (ICNICONSMCL'06), 2006. International Conference on Morne, Mauritius, Apr. 23-29, 2006, pp. 202-202, XP010914787, ISBN: 978-0-7695-2552-5.
Lubrin, E. et al., "MoteCare: An Adaptive Smart BAN Health Monitoring System," Proceedings of the 24th LASTED International Multi-Conference, Biomedical Engineering, Feb. 15-17, 2006, Innsbruck, Austria, pp. 60-67, vol. 2006, XP009110338.
Oetiker, T., "MRTG—The Multi Router Traffic Grapher," Proceedings of the Systems Administration Conference, 1998 Lisa XII, Dec. 6-11, 1998, pp. 141-147, Boston, Massachusetts, XP002302089.
Office Action dated Dec. 27, 2010 in application No. 08 83 7990.4.
Oxford BioSignals Starts Clinical Tirals in US of BioSign Patient Monitoring Technology., Medical Technology Business Europe, Mar. 3, 2005.
Provision of the Minutes in Accordance with Rule 124(4) EPC in European Application No. 08837990.4 dated Apr. 10, 2012. European Application No. 08837990.4 shares the same specification as the present application.
Riudavets, J. et al., "Multi Router Traffic Grapher (MRTG) for Body Area Network (BAN) Surveillance," WSEAS Transactions on Computers, Dec. 1, 2004, pp. 1856-1862, vol. 3(6), XP009110341, ISSN: 1109-2750.
Summons to Attend Oral Proceedings in European Application No. 08837990.4 dated Dec. 14, 2011. European Application No. 08837990.4 is related to the present application.
WelchAllyn, "Accessories," http://www.monitoring.welchallyn.com/products/accessories/, downloaded and printed from Internet on Nov. 14, 2006 in 1 page.
WelchAllyn, "Acuity® Central Station," http://www.monitoring.welchallyn.com/products/systems/acuitycentral.asp, downloaded and printed from Internet on Nov. 14, 2006 in 1 page.
WelchAllyn, "Acuity® LT Central Station," http://www.monitoring.welchallyn.com/products/systems/acuityLTcentral.asp, downloaded and printed from Internet on Nov. 14, 2006 in 1 page.
WelchAllyn, "Atlas™," http://www.monitoring.welchallyn.com/products/portable/atlas.asp, downloaded and printed from Internet on Nov. 14, 2006 in 1 page.
WelchAllyn, "Centralized Monitoring Systems," http://www.monitoring.welchallyn.com/products/systems/, downloaded and printed from Internet on Nov. 14, 2006 in 1 page.
WelchAllyn, "Centralized Monitoring," http://www.monitoring.welchallyn.com/products/applications/centralized.asp, downloaded and printed from the Internet on Nov. 14, 2006 in 2 pages.
WelchAllyn, "Dedicated Network Monitors," http://www.monitoring.welchallyn.com/products/systems/dedicated.asp, downloaded and printed from Internet on Nov. 14, 2006 in 1 page.
WelchAllyn, "Flexible Monitoring," http://www.monitoring.welchallyn.com/products/systems/flexible.asp, downloaded and printed from Internet on Nov. 14, 2006 in 2 pages.
WelchAllyn, "FlexNet™," http://www.monitoring.welchallyn.com/products/wireless/flexnet.asp, downloaded and printed from Internet on Nov. 14, 2006 in 1 page.
WelchAllyn, "Institution-Wide General Purpose Monitoring," http://www.monitoring.welchallyn.com/products/systems/institution.asp, downloaded and printed from Internet on Nov. 14, 2006 in 1 page.
WelchAllyn, "Micropaq®," http://www.monitoring.welchallyn.com/products/wireless/micropaq.asp, downloaded and printed from Internet on Nov. 14, 2006 in 1 page.
WelchAllyn, "Miltary Field & Hospital," http://www.monitoring.welchallyn.com/products/applications/military.asp, downloaded and printed from Internet on Nov. 14, 2006 in 2 pages.
WelchAllyn, "Mobile Acuity LT™ Central Station," http://www.monitoring.welchallyn.com/products/systems/mobileacuityLTcentral.asp, downloaded and printed from Internet on Nov. 14, 2006 in 1 page.
WelchAllyn, "Motion Tolerant Propaq® CS," http://www.monitoring.welchallyn.com/products/portable/motiontolerantcs.asp, downloaded and printed from Internet on Nov. 14, 2006 in 2 pages.
WelchAllyn, "Networked Acuity®," http://www.monitoring.welchallyn.com/products/systems/acuitynet.asp, downloaded and printed from Internet on Nov. 14, 2006 in 1 page.
WelchAllyn, "Partners," http://www.monitoring.welchallyn.com/products/partners/, downloaded and printed from Internet on Nov. 14, 2006 in 2 pages.
WelchAllyn, "Portable Bedside Monitoring," http://www.monitoring.welchallyn.com/products/applications/portablebed.asp, downloaded and printed from the Internet on Nov. 14, 2006 in 1 page.
WelchAllyn, "Portable Monitors," http://www.monitoring.welchallyn.com/products/portable/, downloaded and printed from Internet on Nov. 14, 2006 in 2 pages.
WelchAllyn, "Process Reegineering," http://www.monitoring.welchallyn.com/products/systems/processreeng.asp, downloaded and printed from Internet on Nov. 14, 2006 in 1 page.
WelchAllyn, "Propaq Encore®," http://www.monitoring.welchallyn.com/products/portable/propaqencore.asp, downloaded and printed from Internet on Nov. 14, 2006 in 2 pages.
WelchAllyn, "Propaq® CS," http://www.monitoring.welchallyn.com/products/portable/propaqcs.asp, downloaded and printed from Internet on Nov. 14, 2006 in 2 pages.
WelchAllyn, "Refurbished Monitors," http://www.monitoring.welchallyn.com/products/portable/refurbished.asp, downloaded and printed from Internet on Nov. 14, 2006 in 1 page.
WelchAllyn, "Resource Library," http://www.monitoring.welchallyn.com/products/wireless/resourcelib.asp, downloaded and printed from Internet on Nov. 14, 2006 in 3 pages.
WelchAllyn, "Spot Vital Signs®," http://www.monitoring.welchallyn.com/products/portable/spotvitalsigns.asp, downloaded and printed from Internet on Nov. 14, 2006 in 1 page.
WelchAllyn, "Transport Monitoring," http://www.monitoring.welchallyn.com/products/applications/transport.asp, downloaded and printed from the Internet on Nov. 14, 2006 in 2 pages.
WelchAllyn, "Vital Signs Monitor 300 Series," http://www.monitoring.welchallyn.com/products/portable/vitalsigns.asp, downloaded and printed from Internet on Nov. 14, 2006 in 2 pages.
WelchAllyn, "Welch Allyn OEM Technologies," http://www.monitoring.welchallyn.com/products/oemtech/, downloaded and printed from Internet on Nov. 14, 2006 in 1 page.

(56) References Cited

OTHER PUBLICATIONS

WelchAllyn, "Wireless Propaq® CS," http://www.monitoring.welchallyn.com/products/wireless/wirelesspropaqcs.asp, downloaded and printed from Internet on Nov. 14, 2006 in 2 pages.

WelchAllyn, "Wireless/Telemetry Monitoring," http://www.monitoring.welchallyn.com/products/wireless/, downloaded and printed from Internet on Nov. 14, 2006 in 1 page.

WelchAllyn, Care Units, http://www.monitoring.welchallyn.com/products/careunits/, Nov. 14, 2006, pp. 5.

WelchAllyn, Monitoring Applications, http://www.monitoring.welchallyn.com/products/applications/, Nov. 14, 2006, pp. 2.

Welchallyn Product Overview, http://www.monitoring.welchallyn.com/products/, Nov. 14, 2006, pp. 2.

U.S. 8,845,543, 9/2014, Diab et al. (withdrawn).

International Search Report and Written Opinion for International Application No. PCT/US2008/079643, Apr. 1, 2009.

Capuano et at. "Remote Telemetry—New Twists for Old Technology." Nursing Management. vol. 26, No. 7. Jul. 1995.

DeVita, Michael A., MD, "Medical Emergency Teams: A Vision of the Future," Critical Connections, Feb. 2005, pp. 12-13.

European Office Action for EP application No. 08837990.4 dated Dec. 27, 2010.

Grundy et al. "Telemedicine in Critical Care: An Experiment in Health Care Delivery." Oct. 1977.

Grundy et al. "Telemedicine in Critical Care: Problems in design, implementation and assessment." vol. 10, No. 7. Jul. 1982.

International Search Report and Written Opinion mailed Apr. 1, 2009 regarding PCT/US2008/079643.

Kang, Ho Hyun et al., "Wired/Wireless Integrated Medical Information Prototype System Using Web Service," Enterprise Networking and Computing in Healthcare Industry, 2005, Healthcom 2005, Proceedings of 7th International Workshop on Busan, South Korea , Jun. 23-25, 2005, Piscataway, NJ, USA, pp. 41-44. ISBN: 0-7803-8940-9.

Lubrin et al., An Architecture for Wearable, Wireless, Smart Biosensors: The MoreCare Prototype, Networking International Conference on Systems and International Conference on Mobile Communications and learning Technologies, Apr. 2006, pp. 202, Piscataway, NJ, USA.

WelchAllyn, "Accessories," http:www.monitoring.welchallyn.com/products/accessories/, downloaded and printed from Internet on Nov. 14, 2006 in 1 page.

\* cited by examiner

400

410 {
```
<HEADER>
    <START TIME>1241070389</START TIME>
    <STOP TIME>1241070589</STOP TIME>
    <STEP INTERVAL>30 SEC</STEP INTERVAL>
    <NUM PARAMS>7</NUM PARAMS>
    <PARAM LIST>SPO2,BPM,PI,PVI,SPHB,SPMET,SPCO2</PARAM LIST>
</HEADER>
```

SYSTEMS AND METHODS FOR STORING, ANALYZING, RETRIEVING AND DISPLAYING STREAMING MEDICAL DATA

PRIORITY

The present application is a continuation of U.S. patent application Ser. No. 12/904,925, filed Oct. 14, 2010, issuing as U.S. Pat. No. 8,310,336 on Nov. 13, 2012, which is a continuation-in-part of U.S. application Ser. No. 12/249,806, filed Oct. 10, 2008, now U.S. Pat. No. 8,274,360, which is a non-provisional of U.S. Provisional Application No. 60/979,531, filed Oct. 12, 2007, the disclosures of which are hereby incorporated by reference in their entirety. The present application includes subject matter related to U.S. application Ser. No. 12/904,377, filed Oct. 14, 2010, Ser. No. 12/717,081, filed Mar. 3, 2010 and U.S. Provisional Nos. 61/296,439, filed Jan. 19, 2010 and 61/209,147 filed Mar. 4, 2009, which are also expressly incorporated by reference in their entireties.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters such as blood oxygen saturation level, respiratory rate, and the like. Clinicians, including doctors, nurses, and other medical personnel, use the physiological parameters obtained from patient monitors to diagnose illnesses and to prescribe treatments. Clinicians also use the physiological parameters to monitor patients during various clinical situations to determine whether to increase the level of medical care given to patients.

Many patient monitoring devices provide an alarm function that triggers an alarm when certain physiological parameters exceed safe thresholds. Situations giving rise to an alarm might include, for example, decreased heart rate, respiratory rate, or low blood oxygen saturation levels. Alarms enable clinicians to respond rapidly to possible life-threatening situations. Alarms may be audible, visual, or transmitted over a network to locations in a hospital where clinicians are not in direct view of a patient. Alarms and other physiological information are often transmitted to a central nurses' station or the like, where nurses or other clinicians can monitor several patients at once.

SUMMARY OF CERTAIN EMBODIMENTS

In some embodiments, in a multi-patient monitoring environment having a plurality of patient monitoring devices in communication with one or more clinician monitoring stations, a method of storing streaming physiological information obtained from a medical patient includes: by a computer system comprising computer hardware: receiving identification information from a patient monitor over a network, the patient monitor comprising one or more processors operative to process physiological data obtained from one or more sensors coupled to a medical patient and generate a corresponding data stream at a predetermined data rate; in response to receiving the identification information, retrieving parameter descriptors corresponding to the patient monitor based at least partly on the identification information, each parameter descriptor operative to identify a parameter measurable by the patient monitor and the predetermined data rate; creating a round-robin database (RRDB) file comprising a header, the header comprising the parameter descriptors; receiving the data stream from the patient monitor; and storing the physiological data in records of the RRDB file.

In certain embodiments, in a patient monitoring devices configured to monitor one or more physiological parameters associated with a medical patient, a method of storing streaming physiological information includes: by a patient monitor comprising one or more processors operative to process physiological data obtained from one or more sensors coupled to a medical patient and generate a corresponding data stream at a predetermined data rate: creating a round-robin database (RRDB) file comprising a header and records, the header comprising one or more parameter descriptors operative to identify one or more parameters measurable by the patient monitor, each parameter measurable at a predetermined data rate; generating a data stream in response to one or more signals received from the one or more sensors coupled to the medical patient; and storing the data stream in the records of the RRDB file.

Additionally, in various embodiments, a system for storing streaming physiological information obtained from a medical patient includes: a network management module operative to: receive identification information from a patient monitor over a network, the patient monitor comprising one or more processors operative to process physiological data obtained from one or more sensors coupled to a medical patient and generate a corresponding data stream data at a predetermined data rate; and receive the data stream from the patient monitor, the data stream, comprising parameter descriptors operative to identify the physiological data; a round-robin database (RRDB) component operative to, in response to receiving the identification information from the network management module: receive the data stream from the patient monitor; create an RRDB file comprising a header, the header comprising the parameter descriptors; and use the predetermined data rate to map the data stream to locations in the RRDB file.

In other embodiments, in a multi-patient monitoring environment having a plurality of patient monitoring devices in communication with one or more clinician monitoring stations, a method of retrieving a stream of continuous physiological information associated with a physiological condition of a medical patient stored in a round-robin database includes: providing identification information with a remote retrieval device over a network, the identification information comprising a patient identifier, a physiological parameter, and a review period; receiving a continuous stream of data corresponding to the physiological parameter during the review period of a medical patient associated with the patient identifier; and displaying the continuous stream of data as a waveform on a display of the remote retrieval device.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIG. 4 is a more detailed embodiment of the round-robin database file of FIG. 3;

DETAILED DESCRIPTION

In certain embodiments, systems and methods are provided for rapidly storing and acquiring physiological trend data. For instance, physiological information obtained from a medical patient can be stored in a round-robin database. The round-robin database can store the physiological information in a series of records equally spaced in time. Parameter descriptors may be used to identify parameter values in the records. The parameter values can be dynamically updated by changing the parameter descriptors to provide for a flexible database. In addition, the size of files used in the database can be dynamically adjusted to account for patient condition.

Additionally, in certain embodiments, medical data obtained from a clinical network of physiological monitors can be stored or journaled in a journal database. The medical data can include device events that occurred in response to clinician interactions with one or more medical devices. The medical event data may also include device-initiated events, such as alarms and the like. The medical data stored in the journal database can be analyzed to derive statistics or metrics, which may be used to improve clinician and/or hospital performance.

As used herein the terms "round-robin database" and "RRDB," in addition to having their ordinary meaning, can also describe improved database structures having unique characteristics and features disclosed herein. Sometimes these structures are referred to herein as dynamic RRDBs or adaptive RRDBs.

Figure 1:
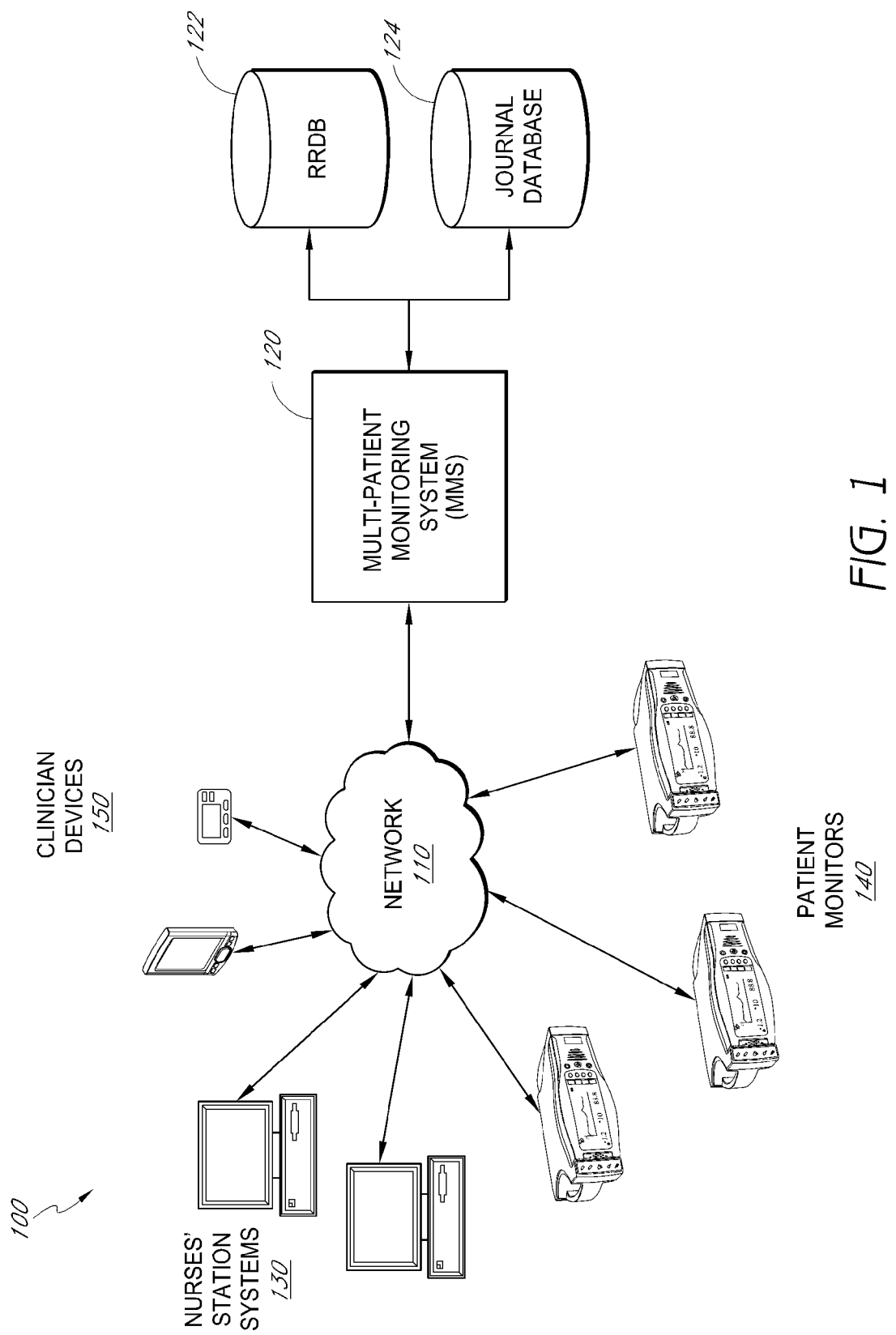
FIG. 1 is a block diagram illustrating an embodiment of a clinical network environment.

FIG. 1 illustrates an embodiment of a clinical network environment 100. The clinical network environment 100 includes a multi-patient monitoring system (MMS) 120 in communication with one or more patient monitors 140, nurses' station systems 130, and clinician devices 150 over a network 110. In certain embodiments, the MMS 120 provides physiological data obtained from the patient monitors 140 to the nurses' station systems 130 and/or the clinician devices 150. Additionally, in certain embodiments, the MMS 120 stores physiological information and medical event information for later analysis.

The network 110 of the clinical network environment 100 can be a LAN or WAN, wireless LAN ("WLAN"), or other type of network used in any hospital, nursing home, patient care center, or other clinical location. For ease of illustration, the remainder of this specification will describe clinical environments in the context of hospitals; however, it should be understood that the features described herein may also be employed in other clinical locations or settings. In some implementations, the network 110 can interconnect devices from multiple hospitals or clinical locations, which may be remote from one another, through the Internet, a leased line, or the like. Likewise, the various devices 120, 130, 140, and 150 of the clinical network environment 100 may be geographically distributed (e.g., among multiple hospitals) or co-located (e.g., in a single hospital).

The patient monitors 140 may be point-of-care (POC) instruments or the like that monitor physiological signals detected by sensors coupled with medical patients. The patient monitors 140 may process the signals to determine any of a variety of physiological parameters. One example of a physiological parameter is blood oxygen saturation ($SpO_2$). Other examples of physiological parameters are described below with respect to FIG. 2.

The patient monitors 140 can provide the physiological information to the MMS 120. The patient monitors 140 can also provide information on medical events, such as alarms, to the MMS 120. Alarms can be triggered, for example, in response to a physiological parameter falling outside of a normal range. Alarms can also include alerts regarding equipment failures, such as a probe-off condition where a sensor has fallen off of a patient. Other examples of medical events are described below with respect to FIG. 2.

In various embodiments, the patient monitors 140 provide the physiological information and medical events to the MMS 120. The MMS 120 is described in greater detail below. In some implementations, the patient monitors 140 may provide at least some of this information directly to the nurses' station systems 130 and clinician devices 150.

The nurses' station systems 130 can be desktop computers, laptops, work stations, or the like that are located at a nurses' station. One or more nurses' station computers 130 can be located at a single nurses' station. The nurses' station computers 130 can receive and display physiological information and alarm data received from the MMS 120 (or monitors 140). In certain embodiments, the nurses' station computers 130 use a graphical user interface (GUI) that provides a streamlined, at-a-glance view of physiological and medical information. An example of this GUI is described below with respect to FIG. 7.

The clinician devices 150 can include any of a variety of devices used by clinicians, such as pagers, cell phones, smart phones, personal digital assistants (PDA), laptops, tablet PCs, personal computers, and the like. The clinician devices 150 are able to receive, in some embodiments, physiological information and alarms from the MMS 120 (or monitors 140). Physiological and alarm data can be provided to a particular clinician device 150, for example, in response to an alarm. The clinician devices 150 can, in some instances, receive values and waveforms of physiological parameters.

Any device in communication with the clinical network environment 100, including but not limited to nurses' station systems 130, 230 patient monitors 140, 240, clinician devices 150, monitors, displays, workstations, a user interface, etc., can be configured to retrieve stored information from the MMS 120, 220 and RRDB 122, 222. In some embodiments, such devices utilize data caching techniques and/or communication hardware to increase the communication speed between such devices and the clinical network environment 100.

The MMS 120 in certain embodiments includes one or more physical computing devices, such as servers, having hardware and/or software for managing network traffic in the network 110. This hardware and/or software may be logically and/or physically divided into different servers 120 for different functions, such as communications servers, web servers, database servers, application servers, file servers, proxy servers, and the like.

The MMS 120 can use standardized protocols (such as TCP/IP) or proprietary protocols to communicate with the patient monitors 140, the nurses' station computers 130, and the clinician devices 150. In one embodiment, when a patient monitor 140 wishes to connect to the MMS 120, the MMS 120 can authenticate the patient monitor 140 and provide the monitor 140 with context information of a patient coupled to the monitor 140. Context information can include patient demography, patient alarm settings, and clinician assignments to the patient, among other things. Examples of context information are described in U.S. application Ser. No. 11/633,656 filed Dec. 4, 2006, titled "Physiological alarm notification system," the disclosure of which is hereby incorporated by reference in its entirety. The MMS 120 may obtain this context information from the nurses' station systems 130 or other hospital computer systems, where patient admitting information is provided.

Upon connecting to a patient monitor 140, the MMS 120 may receive physiological information and medical events from the patient monitors 140. The MMS 120 may provide at least a portion of the physiological information and events to the nurses' station systems 130 and/or clinician devices 150. For example, the MMS 120 may provide physiological data and alarms for a plurality of patient monitors 140 to a nurses' station system 130, where nurses can evaluate the data and/or alarms to determine how to treat patients. Similarly, the MMS 120 may send wireless pages, emails, instant messages, or the like to clinician devices 150 to provide clinicians with physiological data and alarms.

Advantageously, in certain embodiments, the MMS 120 can store physiological information obtained from the patient monitors 140 in a round-robin database (RRDB) 124. The RRDB 122 of various embodiments includes a streamlined database structure that facilitates rapidly storing and retrieving patient data. The RRDB 122 can therefore be used in certain embodiments to rapidly provide physiological trend data to the nurses' stations 130 and to the clinician devices 150. Thus, for example, if a clinician desires to see a patient's physiological trends over a certain time period, such as the past hour, the clinician can use a nurses' station computer 130 or clinical device 150 to query the MMS 120. The MMS 120 may then obtain physiological information corresponding to the desired time period from the RRDB 122. Advantageously, the RRDB 122 can enable faster acquisition of trend data then is possible with relational databases currently used by hospital monitoring systems. Additional uses and optimizations of the RRDB 122 are described below.

In certain embodiments, the MMS 120 also archives or stores information about medical events received from one or more or all devices attached to the network 110 in a journal database 124. The medical events can include events recorded by devices such as the patient monitors 140, nurses' station systems 130, and clinician devices 150. In particular, the medical events can include device events that occur in response to a clinician's interaction with a device, such as a clinician-initiated deactivation of an alarm. The medical events can also include device events that occur without a clinician's interaction with the device, such as the alarm itself. Additional examples of medical events are described below with respect to FIG. 2.

The MMS 120 may analyze the medical event information stored in the journal database 124 to derive metrics, measurement, and/or statistics about the medical events. For example, the MMS 120 can analyze alarm events and alarm deactivation events to determine clinician response times to alarms. Using this derived information, the MMS 120 may generate reports about clinician and/or hospital performance. Advantageously, in certain embodiments, this derived information and/or reports may be used to improve the performance of clinicians and hospitals.

For instance, in certain situations, the reports might help hospitals discover the cause of issues with patient monitors 140. The following example scenario can illustrate potential benefits of such a report. $SpO_2$ alarm levels tend to be different for adults and neonates. However, some clinicians may not know this and may modify neonate $SpO_2$ monitors to include adult alarm levels. These changes can result in many false alarms, which may cause clinicians to become frustrated and avoid using the patient monitors 140. By journaling medical events such as clinician alarm changes, it can be determined by an analysis of the journaled data that clinicians were inappropriately adjusting alarm settings on neonate monitors. A hospital could then use this information to take corrective action, such as by fixing the alarm limits and training the clinicians.

The journaling functionality of the MMS 120 uniquely provides a global, enterprise-wide reporting system that permits executive decision-making with respect to safety and quality management issues within an entire patient care facility. For example, instead of merely reviewing the performance of a particular nurse with respect to a particular bedside device, the MMS 120 is configured to analyze an entire facility at the global or enterprise-wide level. The MMS 120 is able to assess, among other things, the practices of an entire unit within a healthcare facility, such as whether the device's alarms were set to the appropriate levels, how long it took the unit, or a particular shift, or a particular nurse, to respond to an alarm, under what conditions the device alarmed, etc. Such functionality allows healthcare executives responsible for facility-wide quality and safety practices to centrally observe, analyze, and correct healthcare professional performance in real time.

For example, journaled data may be used to generate reports to show how many patient monitor alarms were set outside of the physiologic norms during a particular time period (e.g., during a particular shift), as well as how long it takes (e.g., average time or a range of times) for a critical alarm to be answered, and how often such events occur. Journaled information can be analyzed for a particular time period or for a particular healthcare provider (e.g., nurse). Such journaled information can be helpful to identify personnel who need additional training.

Furthermore, in some embodiments, the MMS 120 is configured to automatically adjust the alarm levels of one or more network-attached devices, such as nurses' station systems 130, patient monitors 140, and/or clinician devices 150 based on the journaled information. For example, in one embodiment, the MMS 120 is programmed to periodically review response time by a particular healthcare practitioner. If the response time exceeds a particular threshold, the MMS 130 modifies a device's alarm setting by increasing its volume level, changing its tone, or by raising (or lowering) the alarm's threshold level.

Although not shown, administrative devices may be provided in the clinical network environment 100. The administrative devices can include computing devices operated by hospital administrators, IT staff, or the like. Using the administrative devices, IT staff may, for example, promulgate changes to a plurality of patient monitors 140, nurses' station systems 130, and the MMS 120. The administrative devices may also allow IT staff to interface third-party systems with the MMS 120, such as electronic medical record (EMR) systems. The third party systems may be used, for instance, to change alarm settings on a plurality of monitors from an administrative device. Actions performed by administrators, IT staff, and administrative devices in general may also be journaled in the journal database 124.

Figure 2:
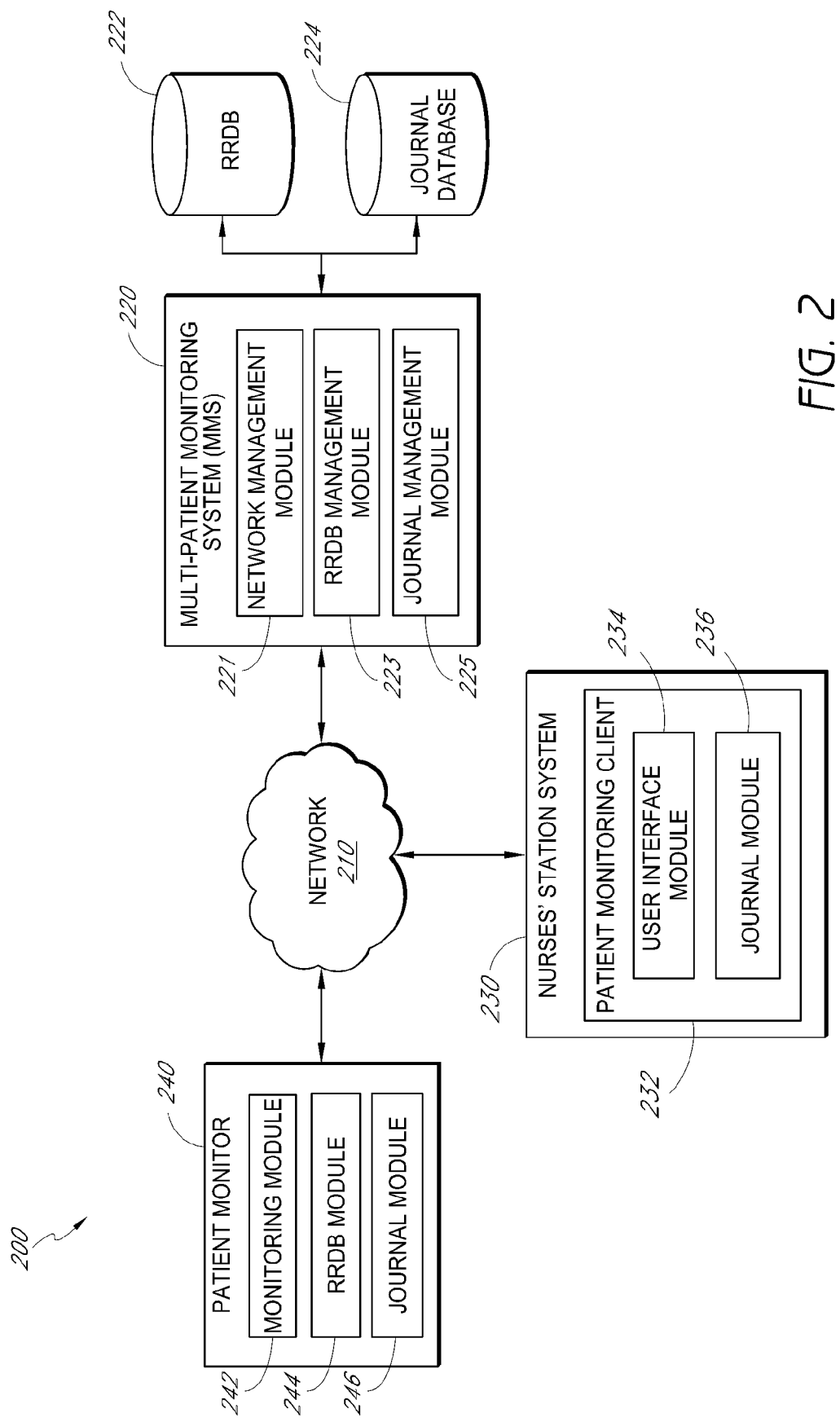
FIG. 2 is a block diagram illustrating a more detailed embodiment of the clinical network environment of FIG. 1.

FIG. 2 illustrates a more detailed embodiment of a clinical network environment 200. The clinical network environment 200 includes a network 210, a patient monitor 240, a nurses' station system 230, an MMS 220, an RRDB 222, and a journal database 224. These components may include all the functionality described above with respect to FIG. 1. One monitor 240 and nurses' station system 230 are shown for ease of illustration. In addition, although not shown, the clinician devices 150 described above may also be included in the clinical network environment 200.

The depicted embodiment of the patient monitor 240 includes a monitoring module 242, an RRDB module 244, and a journal module 246. Each of these modules may include hardware and/or software. Other components, such as a communications module, are not shown but may be included in the patient monitor 240 in various implementations.

The monitoring module 242 can monitor physiological signals generated by one or more sensors coupled with a patient. The monitoring module 242 may process the signals to determine any of a variety of physiological parameters. For example, the monitoring module 242 can determine physiological parameters such as pulse rate, plethysmograph waveform data, perfusion index, and values of blood constituents in body tissue, including for example, arterial carbon monoxide saturation ("HbCO"), methemoglobin saturation ("HbMet"), total hemoglobin ("HbT" or "SpHb"), arterial oxygen saturation ("$SpO_2$"), fractional arterial oxygen saturation ("$SpaO_2$"), oxygen content ("$CaO_2$"), or the like.

In addition, the monitoring module 242 may obtain physiological information from acoustic sensors in order to determine respiratory rate, inspiratory time, expiratory time, inspiration-to-expiration ratio, inspiratory flow, expiratory flow, tidal volume, minute volume, apnea duration, breath sounds, rales, rhonchi, stridor, and changes in breath sounds such as decreased volume or change in airflow. In addition, in some cases the monitoring module 242 monitors other physiological sounds, such as heart rate (e.g., to help with probe-off detection), heart sounds (e.g., S1, S2, S3, S4, and murmurs), and changes in heart sounds such as normal to murmur or split heart sounds indicating fluid overload. Moreover, the monitoring module 242 may monitor a patient's electrical heart activity via electrocardiography (ECG) and numerous other physiological parameters.

In some implementations, the patient monitors 140 may also determine various measures of data confidence, such as the data confidence indicators described in U.S. Pat. No. 7,024,233 entitled "Pulse oximetry data confidence indicator," the disclosure of which is hereby incorporated by reference in its entirety. The patient monitors 140 may also determine a perfusion index, such as the perfusion index described in U.S. Pat. No. 7,292,883 entitled "Physiological assessment system," the disclosure of which is hereby incorporated by reference in its entirety. Moreover, the patient monitors 140 may determine a plethysmograph variability index (PVI), such as the PVI described in U.S. Publication No. 2008/0188760 entitled "Plethysmograph variability processor," the disclosure of which is hereby incorporated by reference in its entirety. The parameters described herein are merely examples, and many other parameters may be used in certain embodiments.

In certain embodiments, the RRDB module 244 receives physiological information from the monitoring module 242 and transmits the physiological information over the network 210 to the MMS 220. In response, as will be described in greater detail below, the MMS 220 may store the physiological information in the RRDB 222. Advantageously, in certain embodiments, the RRDB module 244 associates the physiological information with parameter descriptors prior to transmittal to the MMS 220. The parameter descriptors may be identifiers that the RRDB module 244 associates with each measured physiological parameter value. The MMS 220 may use these parameter descriptors to identify the types of measured parameters received from the RRDB module 244.

The parameter descriptors may be descriptors generated according to a markup language specification, such as an extensible markup language (XML) specification. As such, the parameter descriptors may include tags that enclose measured physiological values. These tags may be machine readable or human readable. For instance, the tags may include numerical identifiers (e.g., "0017") or descriptive identifiers, such as "SPO2" or "SPHB." A simplified example stream of physiological information from an $SpO_2$ sensor and an SpHb sensor associated with parameter descriptors might be as follows: <SPO2>96</SPO2> <SPHB>14.1</SPHB> <SPO2>97</SPO2> <SPHB>14.0</SPHB>, and so on.

In one embodiment, the RRDB module 244 may have stored (e.g., in a data file) a set of predefined parameter descriptors available for the patient monitor 240. These parameter descriptors may correspond to possible parameters that may be measured by the patient monitor 240. The parameter descriptors transmitted by the RRDB module 244 may depend on the particular subset of parameters measured by the patient monitor 240.

If an additional (or different) parameter is subsequently measured by the patient monitor 240, the RRDB module 240 may dynamically update the parameter descriptors that are sent to the MMS 220. Likewise, if the patient monitor 240 ceases to measure one of the parameters, the RRDB module 244 may cease to transmit the corresponding parameter descriptor to the MMS 220.

The patient monitor 240 also includes a journal module 246 in the depicted embodiment. The journal module 240 may record medical events related to the patient monitor 240. These medical events can include clinician-initiated events, such as changes to alarm settings (e.g., maximum and minimum permitted parameter values), types of parameters monitored/sensors connected to the patient monitor 240, and the like. The journal module 246 may record these events by, for example, acting as a key logger or the like to record button presses of a clinician. The journal module 246 may also include current-sense circuitry to detect when sensors or cables are connected to the monitor 240, and so forth. The medical events may also include non-clinician initiated events, such as alarms and alerts. The medical events can also include events from administrative devices (not shown), such as EMR updates to alarm settings across the network 210.

The journal module 246 may log these events locally at the patient monitor 240. In addition, or instead of logging the events locally, the journal module 246 may transmit information about the events to the MMS 220. In turn, the MMS 220 can store the event information in the journal database 224.

The nurses' station system 230 is shown in the depicted embodiment having a patient monitoring client 232. The patient monitoring client 232 can enable the nurses' station system 230 to receive and display physiological information and alarm information. The patient monitoring client 232 includes a user interface module 234. The user interface module 234 may include, for example, software for displaying physiological information, patient information, and medical event information for a plurality of patient monitors 240. The user interface module 234 may also allow clinicians to admit and discharge patients, remotely modify device alarm limits, and the like. An example user interface that may be generated by the user interface module 234 is described below with respect to FIG. 7.

The patient monitoring client 232 further includes a journal module 236. The journal module 236 may include software for recording medical events related to the patient monitoring client 232. For example, the journal module 236 may record which clinicians login to and logoff of the patient monitoring client 232 and when these events occur; admit and discharge events; and other clinician keystrokes, mouse clicks, and interactions with the patient monitoring client 232. The journal module 236 may log this event information locally at the nurse's station system 230 and/or transmit the event information to the MMS 220.

As shown, the MMS 220 may include a network management module 221, an RRDB management module 223, and a journal management module 225, each of which may include one or more software components. In one embodiment, the network management module 221 receives messages containing physiological information and medical event data from the patient monitor 240. The network management module 221 can provide at least a portion of this data to the nurses' station system 230 and clinician devices 150 of FIG. 1. The network management module 221 can also provide the physiological information to the RRDB management module 223 and provide the medical event data to the journal management module 225.

In certain embodiments, the RRDB management module 223 stores the physiological information received from the patient monitor 240 in the RRDB 222. When the patient monitor 240 initially connects to the MMS 220, or at another time, the RRDB management module 223 can create one or more RRDB files in the RRDB 222 corresponding to the patient monitor 240. The contents of this file or files may depend on the type of patient monitor 240, which may be defined by the patient monitor's 240 serial number, model number, vendor identifier, combinations of the same, or the like. Specific examples of the structure and contents of RRDB files are described below with respect to FIGS. 3 and 4.

The RRDB management module 223 can also provide physiological trend data stored in the RRDB to the network management module 221 for transmittal to monitors 240, nurses' station systems 230, and/or clinician devices. The RRDB management module 223 may also provide physiological data from the RRDB 222 to the journal management module 225 for purposes described below with respect to FIG. 6B.

The journal management module 225, in certain implementations, receives medical event data from the monitor 240 and the nurses' station system 230 and stores this data in the journal database 224. In an embodiment, the journal database 224 is a relational database; however, other structures may be used. Each entry of event data may have a corresponding time stamp that indicates when an event occurred. This time stamp may be provided by the journal modules 246 or 236 or by the journal management module 225. The journal management module 225 may also store event counters in the journal database 224 that reflect a number of times medical events occurred. For example, counters could be stored that count how many alarms occurred within a period of time or how many times a clinician logged on or logged off of a network device.

Advantageously, the journal management module 225 may, in certain embodiments, analyze the medical data in the journal database 224 to determine statistics or metrics of clinician and/or hospital performance. The journal management module 225 may provide an interface to users of the nurses' station system 230 or another computing device to access these statistics. In one example embodiment, journal management module 225 can analyze alarm events and alarm deactivation events to determine clinician response times to alarms. The journal management module 225 may further determine the clinician response times in nurses' day and night shifts. The journal management module 225 may generate reports of these statistics so that hospital administrators, for example, may determine which shifts perform better than others.

More generally, the journal management module 225 may generate reports about clinician and/or hospital performance by analyzing various statistics derived from data in the journal database 224. One example of a report is a monitoring report card, which grades a given hospital against other hospitals (or nurses' station against nurses' station, and the like) based at least partly on the derived statistics. Advantageously, hospital administrators, clinicians, and the like may use these statistics and reports to improve the clinician and hospital performance.

Some or all of the features of the clinical network environment 200 may be adapted in certain embodiments. For instance, either or both of the journal modules 246 or 236 may perform some or all of the functions of the journal management module 225. Likewise, one or more journal databases 224 may be stored at the patient monitor 240 and/or nurses' work station 230. Similarly, the RRDB module 224 may perform some or all of the functions of the RRDB management module 223, and an RRDB 222 may be stored at the patient monitor 240. In addition, in some implementations, the clinician devices 150 of FIG. 1 may have RRDB and/or journal modules as well. Many other adaptations, configurations, and combinations may be made in other embodiments.

Figure 3:
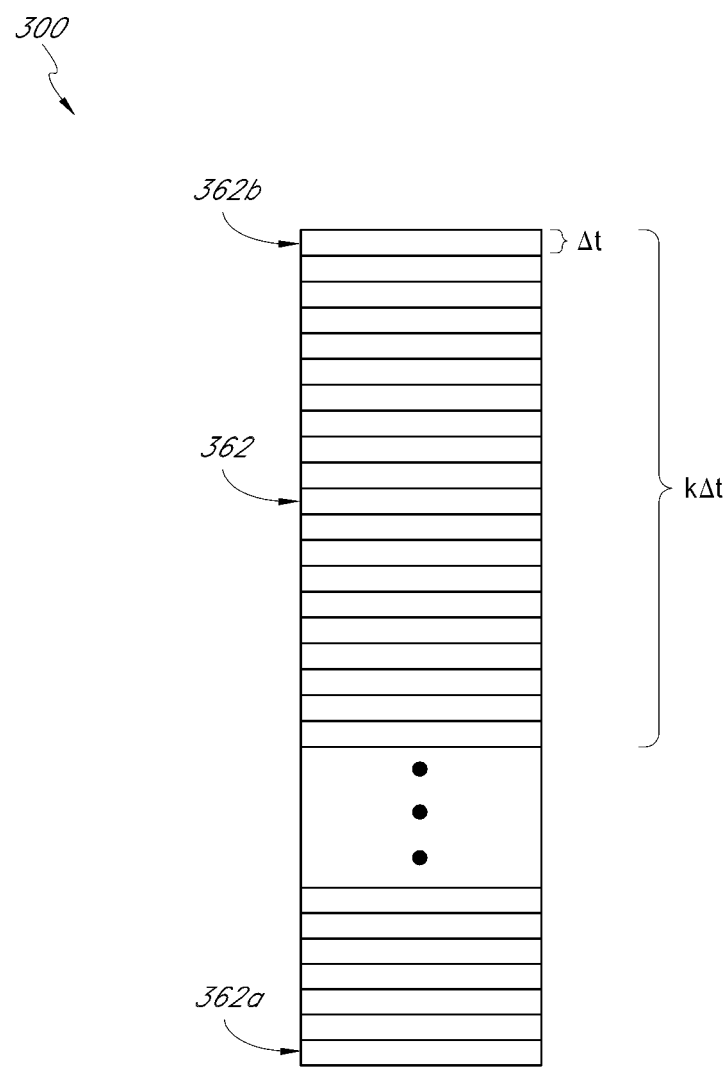
FIG. 3 is a block diagram illustrating an embodiment of a round-robin database file for storing physiological data in the clinical network environment of FIG. 1 or 2.

FIG. 3 illustrates an embodiment of an RRDB file 300 for storing physiological data in a clinical network environment, such as the clinical network environments 100 or 200. By virtue of the configuration of the RRDB file 300, in certain embodiments the MMS 120 or 220 described above can rapidly store and retrieve physiological data.

The RRDB file 300 of certain embodiments has a flat file structure; however, other structures (such as relational structures) may also be used. In an embodiment, a single file 300 corresponds to one patient; however, many files 300 can be used for a single patient. In addition, in some implementations, files 300 can be shared by multiple patients. The RRDB writes physiological information to records 362 in the file 300. In certain embodiments, each record 362 is one line in the RRDB; however, records 362 can include multiple lines. For example, each record 362 could include one or more numbers representing the values of one or more physiological parameters, waveforms, and the like. In addition, in some embodiments, alarm limits and other information may be stored in each record 362.

Advantageously, in certain embodiments, different levels of detail may be stored in RRDB files 300. For instance, a file 300 may be allocated for a single patient, for a device, for a single parameter or technology of the device, or for a channel corresponding to a parameter. Example criteria for allocating these files are described below. The channel may be a value or set of values measured by the device. For example, for an $SpO_2$ sensor, there may be channels for the different wavelengths of light used to obtain the $SpO_2$ reading, e.g., red and infrared (IR) channels. Other optical sensors may have one channel for each wavelength of light used by the sensor (which may be more than two).

In another embodiment, the RRDB stores stream-based data, such as data indicative of a continuously changing physiological parameter of a medical patient. The RRDB advantageously allows such data to be very quickly retrieved and viewed by a remote user, such as over a network and/or the Internet. In addition, because data stored in the RRDB may be retrieved very quickly, in some embodiments the device used to retrieve the data can have only very small (or sometimes no) buffers or local memory. Such devices, sometimes referred to as thin clients, are able to access streaming physiological data from the RRDB over a network with minimal delay and with minimal, perhaps just a transient, memory. Indeed, in some embodiments, the delay is less than 5, 2, or 1 second.

Stream-based data can be obtained from one or more physiological monitors (including patient monitors 140, 240) configured to provide continuous data, or waveforms, indicative of a physiological condition of a medical patient. Different physiological monitors may provide the continuous data at different data rates or frequencies. For example, a first medical device, such as a pulse oximeter, may provide a data stream at 100 Hz (e.g., 100 samples of data per second, or one sample every 10 ms) while a second medical device, such as an EKG may provide a data stream at 250 Hz (e.g., 250 samples of data per second, or one sample every 4 ms).

The MMS 120 or 220 may be configured to open one or more files 300 (as discussed below with respect to FIG. 3) for each data stream. For example, the MMS can create a first RRDB file having consecutive records 362 corresponding to each 10 ms of data received from the first medical device (e.g., which provides data at 100 Hz) and a second RRDB file having consecutive records 362 corresponding to each 4 ms of data received from the second medical device (e.g., which provides data at 250 Hz).

By knowing the time associated with just one single record 362 in a RRDB file (or just the location of the record 362 that corresponds to the current time), the MMS 120, 220 can instantly retrieve large amounts of data corresponding to the physiological condition and associated physiological waveforms of a medical patient during any time period of interest. For example, by providing only the starting time and duration of a period of interest (for example, if a clinician wanted to view 10 seconds of the respiratory waveform of the patient as it was 2 hours ago) the MMS is able to instantly retrieve the associated data. In one embodiment, such performance is attained due to each record 362 of the RRDB file 300 corresponding to a fixed period of time with respect to the records 362 before and after it, and because in some embodiments, the RRDB is continuously updating its current memory location. For example, as discussed above, if the data in the RRDB file 300 was obtained from a device that provides data at 100 Hz, each record 362 in the RRDB file 300 will correspond to 10 ms. If the current position in the RRDB is known, desired data starting and ending locations can be readily determined by simple multiplication operations.

In contrast, typical physiological data systems use relational database structures, which are generally designed to conserve memory and do not provide instantaneous access to large, continuous memory areas. The relational database structure utilizes an index, or pointer table to indicate which discontinuous portions of a memory correspond to data of a particular time period. For example, a relational database's index might indicate that records 6-10 correspond to the first five data samples, records 256-260 correspond to the next five data sample, records 67-71 correspond to the next five data samples, etc. The RRDB avoids the delay associated with querying an index and then moving irregularly within a memory space to find continuous memory streams.

Referring again to FIG. 2, the RRDB module 244 of the patient monitor 240 may provide different amounts of physiological information to the RRDB 222, corresponding to the different types of RRDB files just described. The RRDB module 244 may select a level of detail based at least partly on a health status of the patient. If the patient is relatively healthy, for instance, the RRDB module 244 may send less information to the RRDB 222. In contrast, if the patient is relatively less healthy (e.g., more acute), the RRDB module 244 may send a higher granularity of physiological information to the RRDB 222. In other embodiments, the RRDB module 244 may also adapt the amount of physiological information transmitted to the RRDB 222 based on other factors, such as the degree of noisiness of physiological signals, variability of the signals, and so on.

For example, the MMS 120, 220 may be configured to store physiological information received from patient monitors 140, 240 only if the quality of the data and/or the confidence in the accuracy of the data exceeds a predetermined threshold level. In cases where the quality of the data and/or the confidence in its accuracy does not exceed a predetermined threshold level, the MMS 120, 220 could be configured to write a zero or a flag (e.g., "low quality," "low confidence," etc.) to the RRDB instead of, or in addition to, the data received from a patient monitor 140, 240.

In some embodiments, data from the RRDB (including patient record (See FIG. 4) and waveform data) is written to the patient's electronic medical record ("EMR") (not shown). However, similar quality and/or confidence controls may be applied to such embodiments, as well. For example, the MMS 120, 220 could be configured to send or store such data to the patient's EMR only when the quality of the data and/or the confidence in its accuracy exceeds a predetermined threshold level.

In addition, in some embodiments the RRDB module 244 may instruct the RRDB management module 223 to open a single file for a patient. This file may contain a relatively high level of detail for each device connected to the patient. This setting may be appropriate in circumstances where the patient is relatively healthy. If the patient is less healthy, the RRDB module 244 may instruct the RRDB management module 223 to create a single file for each device connected to the patient. Each of these files may have more detail than may be included in a single file for a patient. Continuing, at lower levels of health, the RRDB module 244 may instruct the RRDB management module 223 to create a file for each parameter measured by the patient monitor 240, or a file for each channel of a sensor (which may include raw data from the sensor). Thus, greater amounts of detail may be provided as the patient's health becomes more acute.

The RRDB module 244 may dynamically adjust the amount of data sent and/or the frequency that data is sent to the RRDB 222 based on the patient's health. As an example, if the patient's SpHb level drops below a safe level (e.g., outside of alarm limits), the RRDB module 244 may send more detailed physiological information to the RRDB 222 or may send physiological information more frequently. In response to receiving additional detail, the RRDB management module 223 may create new files to store the more detailed physiological information. Once the patient's SpHb returns to normal, the RRDB module may send a lower level of detail to the RRDB 222. The RRDB management module 223 may then create a new file to store the lower level of detail, or use a previously-created lower-level detail file. Thus, in certain embodiments, the RRDB module 244 and the RRDB management module 223 may perform adaptive control of RRDB file storage. Thus, in certain embodiments, the RRDB may be considered an adaptive or dynamic RRDB.

Additionally, in certain embodiments, the RRDB module 244 may send multiple streams of physiological data to the RRDB 222. Different streams may have different granularities of physiological data and may be stored in different files in the RRDB 222. For example, each stream of physiological data may include one or more channels of physiological information. Each stream may correspond to one or more files in the RRDB 222.

In some embodiments, adaptive or dynamic RRDB principles are applied to multiple physiological data streams generated from one or more patient monitoring devices. For example, in one embodiment, amount of physiological information transmitted from a first medical device to the RRDB, or from the RRDB module 244 to the RRDB 222, is controlled based upon an acuity level indicated by a second medical device. For instance, in one embodiment, an MMS 120 communicates with one or more patient monitors 140 attached to the same patient. The first patient monitor 140 monitors a first physiological parameter (for example, $SpO_2$) and a second patient monitor attached to the same patient monitors a second physiological parameter (for example, a respiration parameter, such as respiration rate, volume of respiration, etc.). Each monitor 140 streams physiological information to the MMS 120 at a particular data rate. The first physiological monitor 140 streams data at a first data rate and the second physiological monitor 140 streams data at a second data rate. If the MMS 120 determines that either physiological parameter is outside of a predetermined threshold level, it changes (e.g., increases or decreases) the either or both of the first and second data rates. For example, if the MMS 120 determines that the $SpO_2$ level has dropped below a predetermined threshold or alarm level, the MMS 120 sends a command to the second physiological monitor 140 (which is monitoring a respiration parameter) to increase its data rate.

The data rate includes either or both of the rate at which data is sampled from the patient by the physiological monitor 140 as well as the rate at which data is transmitted over the network to the MMS 120. In addition, although the previous example was discussed in terms of two separate physiological monitors 140, the same principles apply to a single physiological monitor 140 configured to monitor more than one physiological parameter of a medical patient (e.g., a monitor 140 configured to measure both $SpO_2$ and a respiration parameter).

Referring again to FIG. 3, the RRDB can store a predetermined number of records 362 in the file 300. After writing data to the last record 362a in the file 300, the RRDB automatically loops back to and overwrites the first record 362b— hence the term "round-robin." The records 362 can be stored at regular (e.g., equal) time intervals, denoted by $\Delta t$ in the FIGURE. As each record 362 is stored in the RRDB, a time stamp can be applied to the record 362. Thus, $\Delta t$ can represent the difference in value between the time stamps of any two sequential records 362. Alternatively, a header section of the file 300 (see FIG. 4) may include a predefined time step that dictates when new values are recorded in the file 300. In some instances, a patient monitor may not send data to the RRDB, either because the monitor ceased to monitor data or because the monitor determines that data need not be recorded (e.g., because the patient is healthy). To preserve the time interval structure when the monitor ceases to send data, zeros or other non-data values (such as NaN—"not a number") can be stored in one or more records 362 of the file 300 in place of physiological information.

To read records 362 from the file 300, a pointer or the like could be instructed to obtain k records, such as the previous k records (e.g., $k\Delta t$). For example, to obtain the first k records 362, a file pointer could be advanced over the most recent k records 362 while the RRDB management module 223 (for instance) reads the k records 362. Any subset of the records 362 can be obtained, including a subset of the most recent records 362 or even all of the records 362. In addition, portions of the records 362 may be read. For example, values for a particular parameter from a plurality of parameters may be read from the previous k records 362.

Advantageously, records 362 can be obtained from the RRDB several orders of magnitude faster than from a relational database. For instance, in one embodiment, searches in the database can be performed as zero-order searches. Thus, physiological information trends can be rapidly streamed or otherwise provided to clinical devices, nurses' station computers, and the like. In some implementations, the RRDB can be configured such that physiological information is read and transmitted to clinical devices fast enough to comply with certain standards promulgated by the Joint Commission on the Accreditation of Healthcare Organizations (JCAHO) for the transmission of alarms. Thus, for example, if a standard required alarms to be transmitted to clinicians within five seconds of the alarm occurring, the RRDB can be configured to provide trend data to the clinician device along with the alarm notification within the five second period.

FIG. 4 illustrates a more detailed embodiment of an RRDB file 400. The RRDB file includes a header 410 and a plurality of records 420. The header 410 includes data that may be used by the RRDB management module 223, for example, to read and write to the file 400, as well as search through the file 400. In the depicted embodiment, fields in the header 410 are denoted by XML tags. This is merely one implementation that may be varied in other embodiments.

The fields in the example header 410 shown include a start time, stop time, step interval, number of parameters, and parameter list. The start and stop times are measured in seconds in the depicted embodiment (e.g., seconds from Unix epoch—Jan. 1, 1970). The step interval (30 seconds in the embodiment shown) indicates how frequently the records 420 are written to the file 400. The number of parameters (in this case, 7) indicates how many physiological parameters are being monitored. The parameter list includes a list of parameter descriptors corresponding to the parameters being monitored. Each of the fields in the header 410 may be adjusted by the RRDB management module 223. Additional or fewer fields may be included in certain embodiments.

Each record 420 in the depicted embodiment is a single line including parameter values separated by a delimiter character (in this case, a space). The parameter values in the first record 420, for example, are 96, 55, 8.9, 14, 14.1, 0.5, and 1.0. These values correspond to the order of the parameter descriptor in the parameter list of the header 410. Thus, the value 96 corresponds to the SPO2 parameter descriptor, the value 55 corresponds to the BPM (beats per minute) parameter descriptor, and so on.

Advantageously, in certain embodiments, because the parameter list in the header 410 includes the parameter descriptors, the records 420 can be written without including the parameter descriptors in the individual records 420. As a result, in certain implementations, the file 400 can have a smaller size than if the parameter descriptors were embedded in the records 420.

Figure 5A:
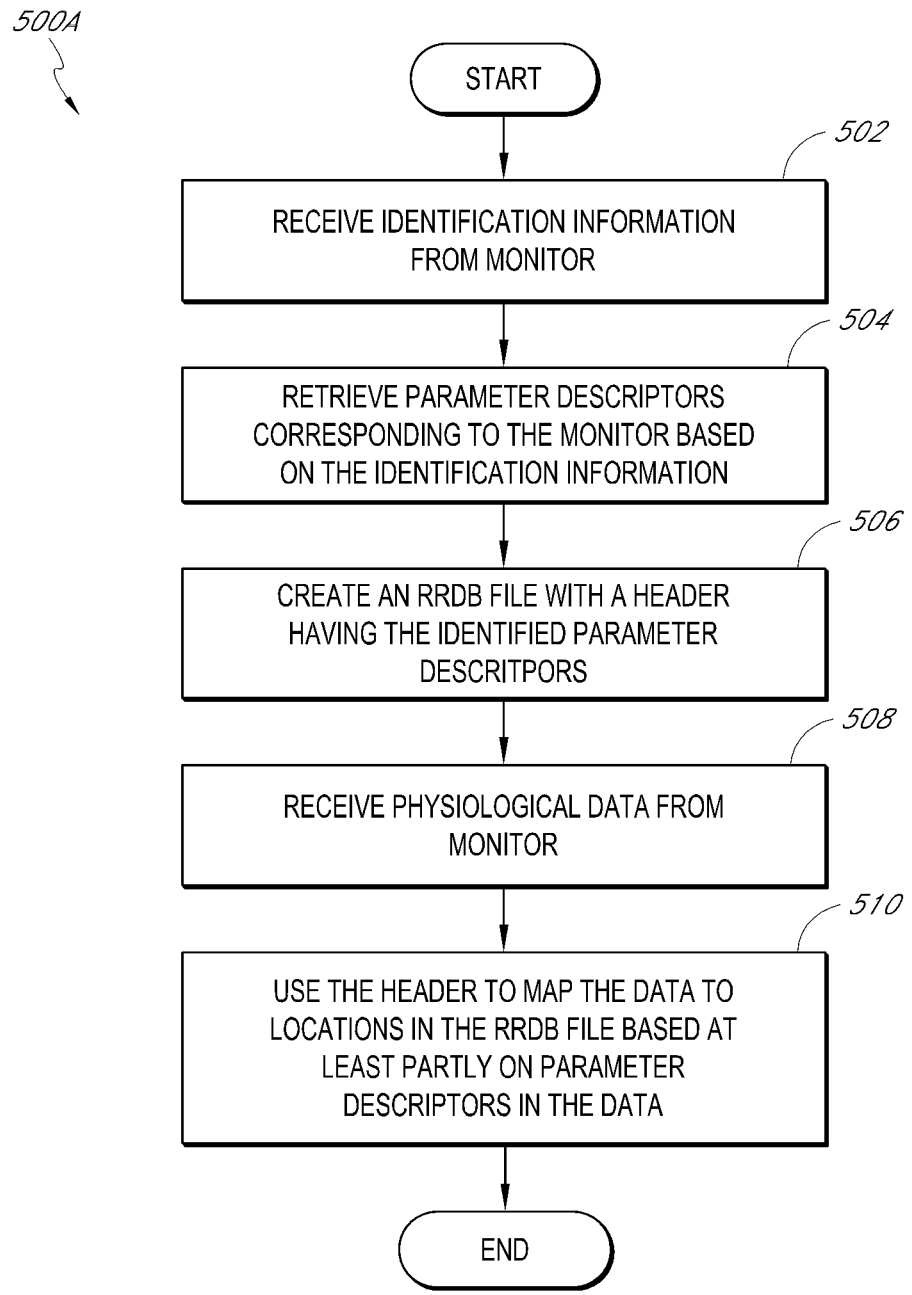
FIGS. 5A through 5C are flow charts illustrating embodiments of processes for using a round-robin database for storing physiological data.
Figure 5B:
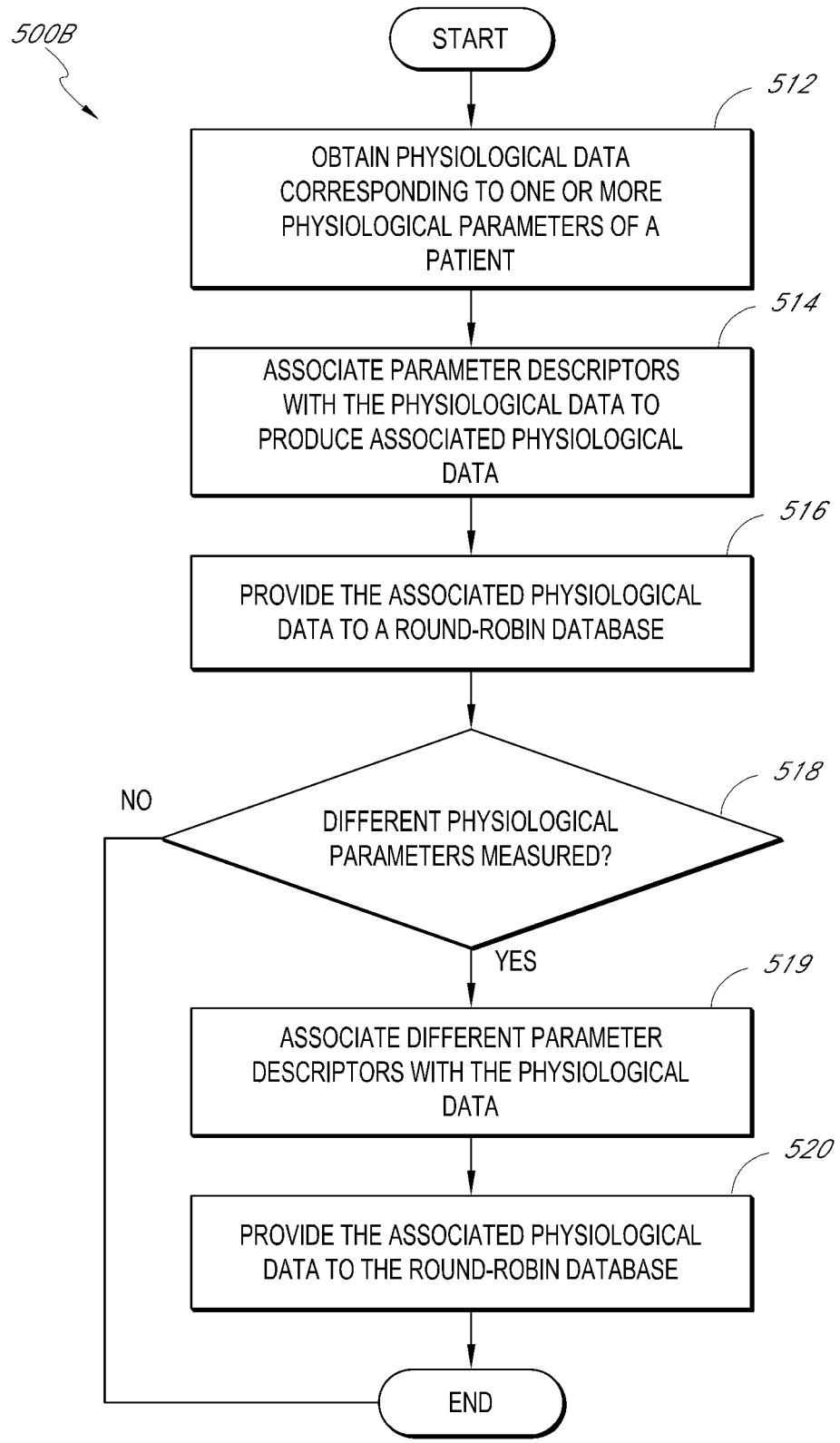
Figure 5C:
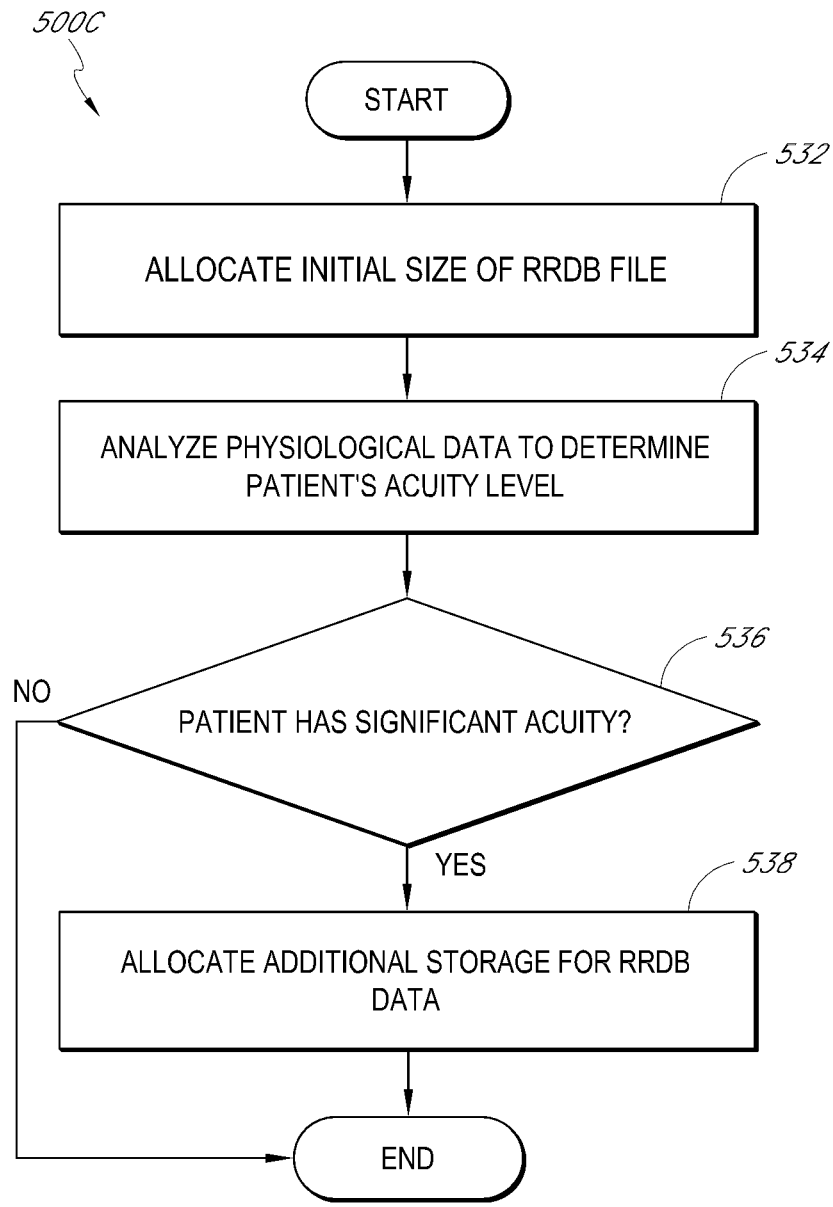

FIGS. 5A through 5C illustrate embodiments of processes 500 for using an RRDB to store physiological data. Referring to FIG. 5A, an embodiment of a process 500A for providing physiological data to an RRDB is shown. In one embodiment, the process 500A may be implemented by any of the MMS's described above (e.g., the MMS 120 or 220). In particular, the process 500A may be implemented by the RRDB management module 223 of FIG. 2. Alternatively, at least some of the blocks may be implemented by the RRDB module 244 of the patient monitor 240. Advantageously, in certain embodiments, the process 500A enables RRDB files to be created for patient monitors that communicate with a MMS over a clinical network.

At block 502, identification information is received from a patient monitor. The identification information may include, for example a serial number of the patient monitor, a model number of the patient monitor, a vendor of the patient monitor, identification of one or more original equipment manufacturer (OEM) modules of the patient monitor, combinations of the same, and the like.

At block 504, parameter descriptors corresponding to the patient monitor are retrieved based at least partly on the identification information. The parameter descriptors for each monitor may be stored in a file on the MMS 120 or 220. For example, a set of possible parameter descriptors may be stored for each monitor serial number, which descriptors correspond to possible parameters that a given monitor can process. In certain embodiments, the parameter descriptors are extensible markup language (XML) descriptors or the like.

An RRDB file with a header having the identified parameter descriptors is created at block 506. An example of a header for an RRDB file is described above with respect to FIG. 4. The parameter descriptors may be inserted, for example, into the parameter list shown in FIG. 4. Thus, the parameter list for a given patient monitor may be determined by the RRDB management module 223. As will be described below with respect to FIG. 5B, the parameter list may also be determined at least partly by the patient monitor.

At block 508, physiological data is received from the patient monitor. At block 510, the header is used to map the physiological data to locations in the RRDB file. This mapping may be performed at least partly by using the descriptors in the data, as described above with respect to FIG. 4.

FIG. 5B illustrates another embodiment of a process 500B for providing physiological data to an RRDB. This process 500B may be implemented by the patient monitor (e.g., 140 or 240). In particular, the RRDB module 244 may perform certain blocks of the process 500B. Alternatively, at least some of the blocks may be implemented by the RRDB module 244 of the patient monitor 240. Advantageously, in certain embodiments the process 500B enables RRDB files to be dynamically created based on changing parameters monitored by the patient monitor.

Physiological data corresponding to one or more physiological parameters of a patient are obtained at block 512. This block may be performed by the monitoring module 242 described above. At block 514, parameter descriptors are associated with the physiological data to produce associated physiological data. This association may be performed by the RRDB module 244. The association may take place in one embodiment by inserting XML tags into the physiological data. The associated physiological data is provided to an RRDB at block 516.

In response to the transmission of this associated physiological data, in one embodiment the MMS can create an RRDB file having the parameter descriptors identified in the physiological data. Alternatively, the MMS may have already created the RRDB file according to the process 500A described above.

At decision block 518, it is determined whether different physiological parameters have been measured. If so, at block 519, different parameter descriptors are associated with the physiological data, and at block 520, the associated physiological data is again provided to the RRDB. Blocks 518-520 may be implemented by the RRDB module 244. As an example, suppose that the parameters measured in block 512 include SpO$_2$ and ECG. The parameter descriptors provided in block 514 might be "SPO2" and "ECG." If a clinician enabled an SpHb parameter measurement on the monitor at block 518, the parameter descriptors associated with the physiological data in block 519 might now include "SPO2" and "ECG" and "SPHB."

In response to the transmission of the new associated physiological data at block 520, the MMS may create a new RRDB file having the new parameter descriptors identified in the physiological data. Thus, the patient monitor may be able to dynamically adjust the physiological data and associated descriptors provided to the RRDB.

FIG. 5C illustrates an embodiment of a process 500C for dynamically adjusting RRDB storage corresponding to a patient monitor. In one embodiment, the process 500C may be implemented by any of the MMS's described above (e.g., the MMS 120 or 220). In particular, the process 500C may be implemented by the RRDB management module 223. Alternatively, at least some of the blocks may be implemented by the RRDB module 244 of the patient monitor 240.

As described above with respect to FIG. 3, the size of an RRDB file may be predetermined and may not increase. This constant size therefore can provide a predetermined storage amount for physiological trend data. The size of the RRDB file may be configured, for example, upon patient admittance to the hospital. An example size of the RRDB might correspond to 72 hours worth of data. For some acute patients, however, additional trend data may be desired. However, because the RRDB file may have a constant size, after the example 72 hours, the trend data will be overwritten. Advantageously, in certain embodiments, the process 500C enables additional trend data to be written to an RRDB. Thus, in certain embodiments, the RRDB may be considered an adaptive or dynamic RRDB.

At block 532, an initial size of an RRDB file is allocated. The initial file size may be chosen based on a projected length of stay of the patient, the patient's current health status, or the like. Alternatively, the file size may be predefined for all patients. At block 534, physiological data received from a patient monitor is analyzed to determine the patient's acuity level. The acuity level of the patient can be determined, for instance, by analyzing the PVI of the patient, which corresponds to variability in the patient's plethysmograph. A patient with higher PVI or variability may benefit from additional trend data. Other values that may be considered in determining acuity level include the data confidence indicators described in U.S. Pat. No. 7,024,233, incorporated above, pulse rate, SpO$_2$ variability, and variation of any other physiological parameter. In addition, in some embodiments, acuity may be determined by examining the patient's alarm history, such that a history of multiple alarms or severe alarms may indicate acuity.

At decision block 536, it is determined whether the patient has significant acuity. If the patient has significant acuity, additional storage for RRDB data is allocated at block 538. This initial storage may be allocated by extending the length of the RRDB file, but creating a new file, or the like. Otherwise, if the patient does not have significant acuity, the process 500C ends.

Figure 6A:
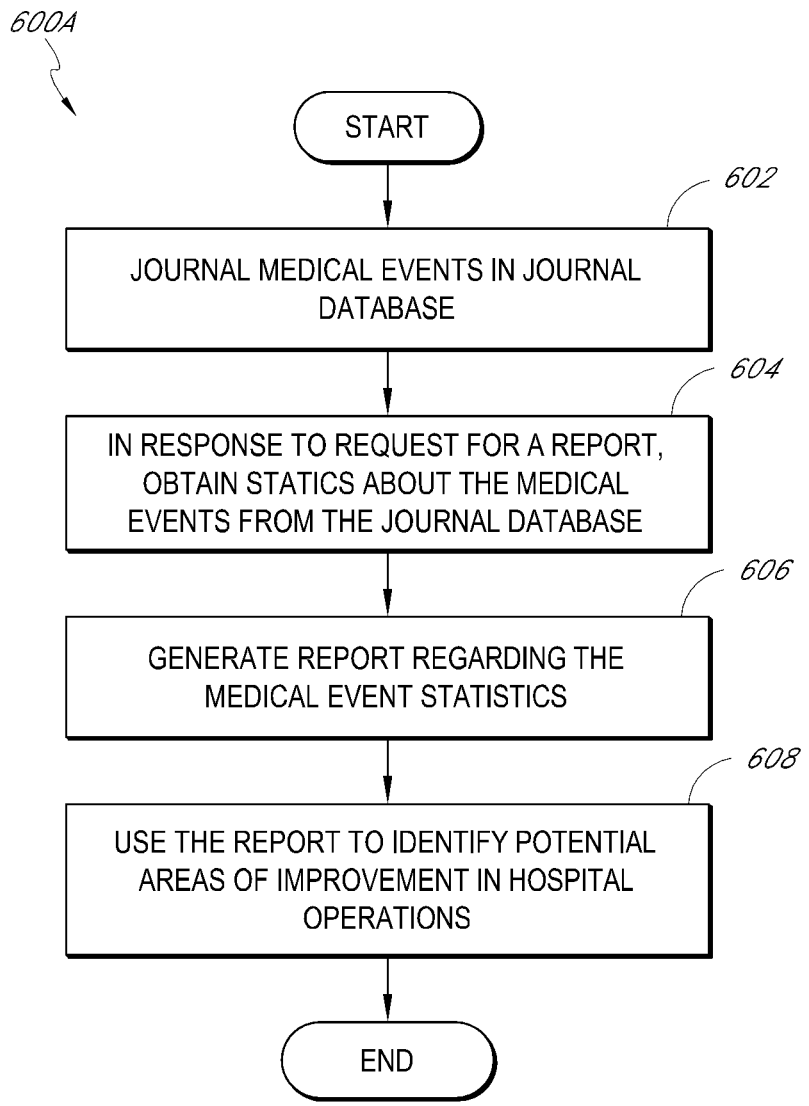
FIG. 6A is a flow chart illustrating an embodiment of a process for journaling medical events in a journal database.

FIG. 6A illustrates an embodiment of a process 600A for journaling medical events in a journal database. In one embodiment, the process 600A may be implemented by any of the MMS's described above (e.g., the MMS 120 or 220). In particular, the process 600A may be implemented by the journal management module 225. Alternatively, at least some of the blocks may be implemented by the journal modules

236, 246. Advantageously, in certain embodiments, the process 600A facilitates the generation of reports based on the journaled data.

At block 602, medical events are journaled in a journal database. In response to requests for report from a user (e.g., a clinician), at block 604 statistics about the medical events are obtained from the journal database. The statistics may include the type, frequency, and duration of medical events, the identity of clinicians or patients associated with the events, alarm response times, combinations of the same, and the like.

A report is generated at block 606 regarding the medical event statistics. At block 608, the report is used to identify potential areas of improvement in hospital operations. For example, the report can be a "monitoring report card" that assigns scores to the hospital or clinicians of the hospital based on their performance.

Figure 6B:
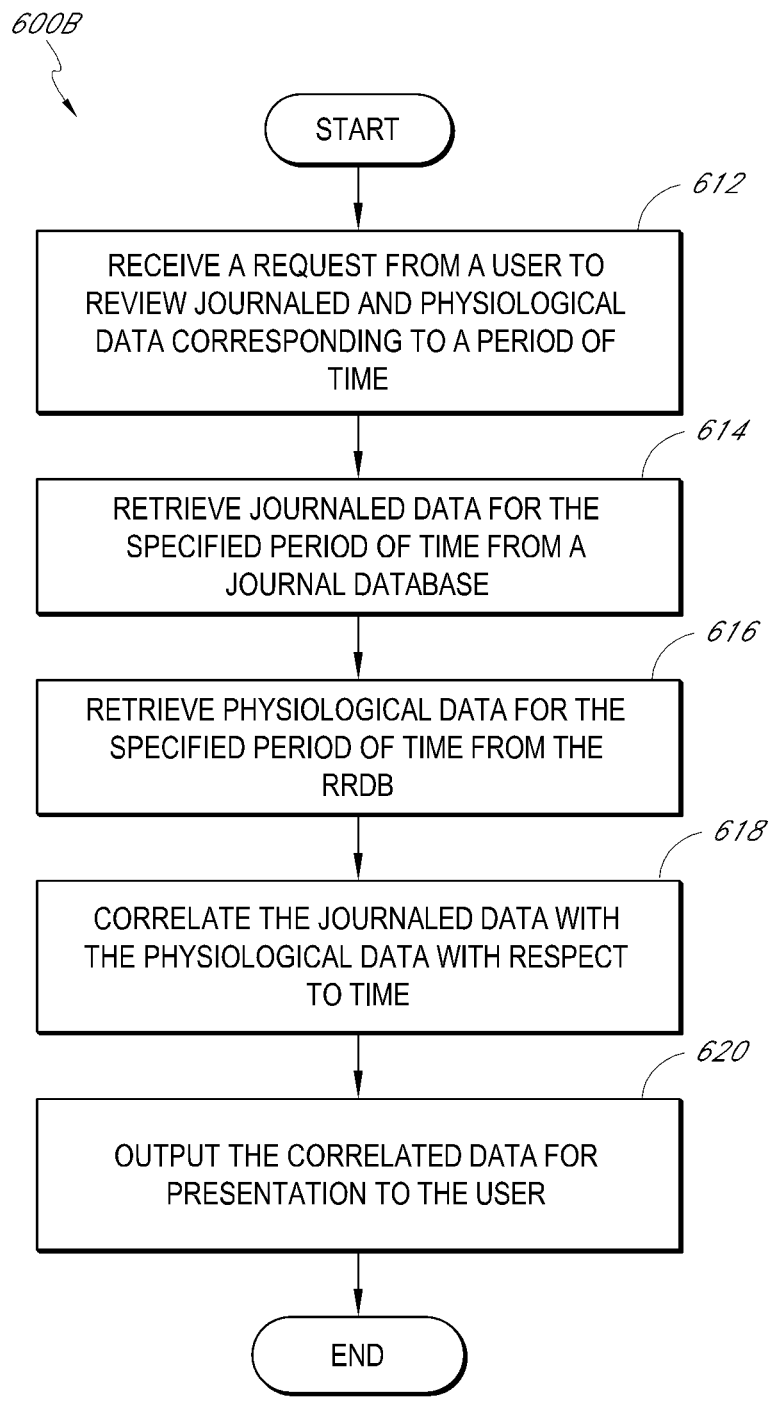
FIG. 6B is a flow chart illustrating an embodiment of a process for correlating data from the journal database and the round-robin database.

FIG. 6B illustrates an embodiment of a process 600B for correlating data from a journal database and an RRDB. In one embodiment, the process 600B may be implemented by any of the MMS's described above (e.g., the MMS 120 or 220). In particular, the process 600B may be implemented by the RRDB module 223 and journal management module 225. Alternatively, at least some of the blocks may be implemented by the RRDB module 244 and journal modules 236, 246. Advantageously, in certain embodiments, the process 600B enables physiological information from the RRDB and medical events to be correlated in time. Such a reconstruction of events and physiological data can be akin to aviation "black box" technology, allowing the user to replay clinical actions leading up to medical incidents.

At block 612, the request is received from a user to review journaled and physiological data corresponding to a period of time. The user may be a clinician, hospital administrator, or the like, who wishes to determine the cause of a problem in the healthcare of a patient. For instance, the user may wish to determine why clinicians failed to respond when a patient's SpO$_2$ dropped below safe levels.

At block 614, journaled data is retrieved for the specified period of time from a journal database. This block may be performed by the journal management module 225. At block 616, physiological data for the specified period of time is retrieved from an RRDB. This block may be performed by the RRDB management module 223. The journal data is correlated with the physiological data with respect to time at block 618. This correlation may include reconstructing a timeline of medical events, with values of physiological parameters (optionally including waveforms) provided in the correct time sequence on the timeline. In some embodiments, to facilitate this coordination between the RRDB management module 223 and the journal management module 225, timestamps in each database 222, 224 may be synchronized when the data is stored.

The correlated data is output for presentation to the user at block 620. The output may include, for example, a graphical view of medical events superimposed on physiological information (e.g., a waveform), or the like. Many display formats may be used for the correlated data.

Figure 7:
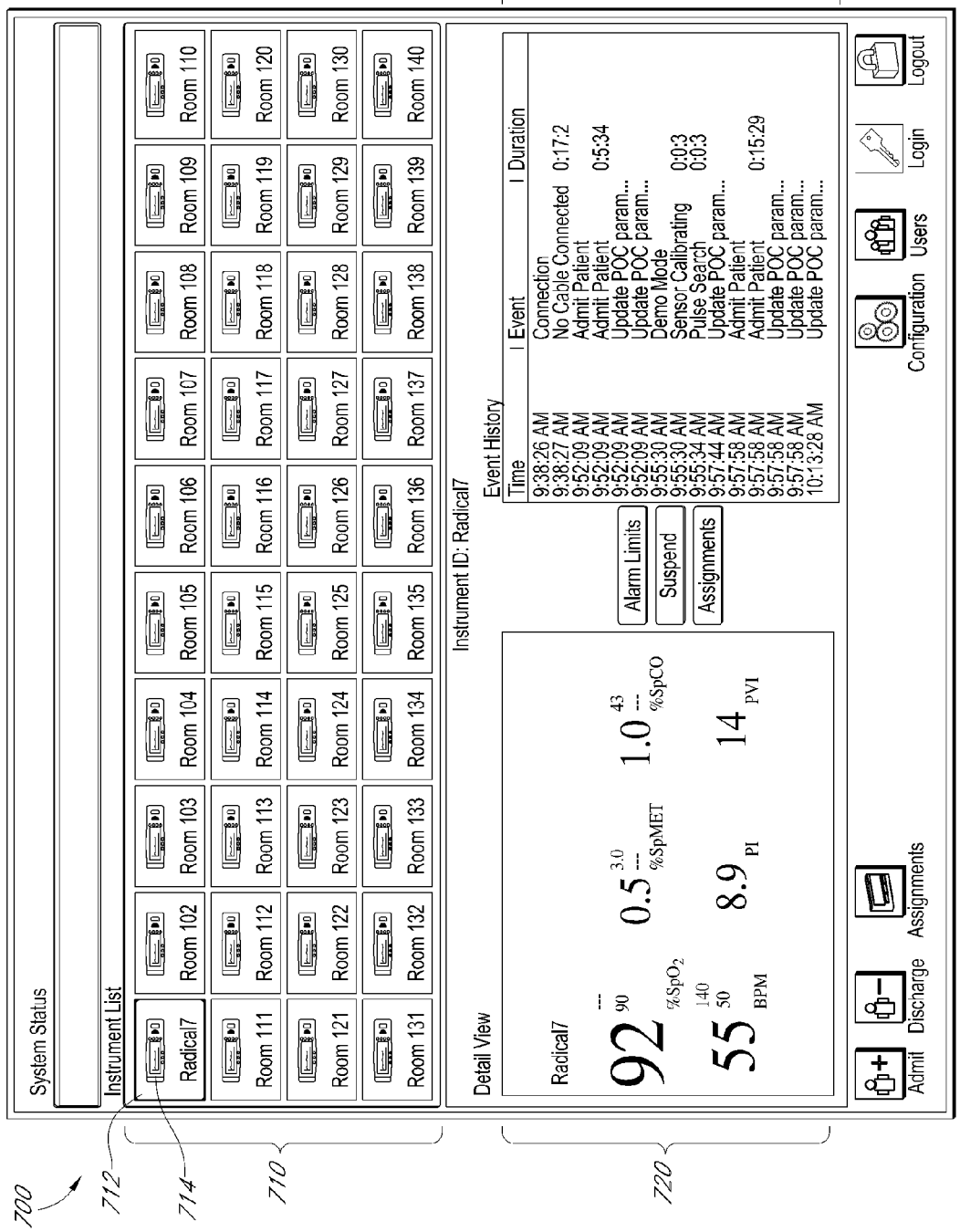
FIGS. 7-11 are screen shots of an example user interface for monitoring patients in the clinical network environment of FIG. 1.

FIG. 7 illustrates an example graphical user interface (GUI) 700 for monitoring patients. The GUI 700 can be provided on a nurses' station system or the like. The GUI 700 can also be displayed on a clinician device. The GUI 700 can be provided on any display. For example, the GUI 700 can be provided over the Internet to a remote user, or on a monitor located within a healthcare treatment facility, such as a hospital, nursing home, patient's home, and/or clinician's home or office.

The GUI 700 includes several display areas. In the depicted embodiment, the GUI 700 includes a patient status display area 710, sometimes referred to as the patient dashboard, or just dashboard. The patient status display area 710 shows the status of multiple patients in a hospital or other clinical location. In an embodiment, patient status display area 710 depicts patient status for patients in a hospital department. Advantageously, in certain embodiments, the patient status display area 710 provides an "at-a-glance" view of multiple patients' health status. The patient status display area 710 can include just a portion of the GUI 700, as shown in FIG. 7. In some embodiments, the entire GUI 700 (or almost the entire GUI 700) is allocated to display the patient status display are 710.

The patient status display area 710 includes a plurality of patient status modules 712. Each patient status module 712 can correspond to a patient monitor that can be coupled to a medical patient. Each patient status module 712 can display a graphical status indicator 714. An example graphical status indicator 714 is shown in the screens 700 as a miniature patient monitor icon. The graphical status indicator 714 can selectively indicate one of several states of a patient monitor. In one embodiment, four possible patient monitor states can be depicted by the graphical status indicator 714. These include an alarm condition, a no alarm condition, patient context information status, and connection status.

In various implementations, the graphical status indicator 714 changes color, shape, or the like to indicate one of the different patient monitor states. For example, if an alarm condition is present, the graphical status indicator 714 could turn red to signify the alarm. If there is no context information available for the patient (see FIG. 1), then the graphical status indicator 714 could turn yellow. If the device is not connected to the patient or the network, then the graphical status indicator 714 could turn gray. And if there is no alarm condition, if there is context information, and if the patient monitor is connected to the patient and the network, then the graphical status indicator 714 could turn green. Many other colors, symbols, and/or shapes could be used in place of or in combination with the above-described embodiments.

Advantageously, the graphical status indicator 714 shows at a glance the status of a patient monitor. Thus, in the patient status display area 710, several graphical status indicators 714 corresponding to several patients show an at-a-glance view for the patient monitors corresponding to these patients. A clinician can therefore readily see the needs that a patient might have with regards to alarms, connection status, and context information.

Currently available graphical user interfaces for nurses' station computers tend to show a plurality of wave forms or changing physiological parameter numbers for each patient. This method of displaying patient information can be cluttered, confusing, and even hypnotic in some situations. Nurses working on a night shift, for instance, may find it difficult to concentrate on an alarm when several other patients' indicators on the display have changing numbers, changing waveforms, or the like. In contrast, in the graphical interface herein described, when the graphical status indicator 714 indicates an alarm condition, this alarm condition can stand out and be immediately recognized by the clinician.

Moreover, the graphical status indicator 714 simplifies the first level of analysis that nurses tend to perform. In currently available devices, nurses often have to analyze waveforms at the nurses' station to determine the health status of a patient. However, using the screens 700, a nurse need not interpret any waveforms or changing parameters of the patient, but instead can rely on the graphical status indicator 714 that indicates the presence of an alarm.

In certain embodiments, the patient status modules 712 can be selected by a single mouse click, touching a screen or monitor displaying the GUI 700, or the like. Selecting a patient status module 712 in one embodiment can bring up a patient monitor view area 720. The patient monitor view area 720 (sometimes referred to as a virtual device screen 720) shows a view of a patient monitor corresponding to a selected patient status module 712. In certain implementations, the patient monitor view area 720 can show a view of the screen from the actual patient monitor device at the bedside of the patient. Thus, a clinician can readily recognize the physiological parameters of the patient in a format that the clinician is likely familiar with. The patient monitor view area 720 is currently receiving physiological information from a patient. The patient monitor view area 720 displays the real-time values of various physiological parameters that are being monitored for a selected patient. In addition, the patient monitor view area 720 displays the name of the parameter (e.g., % $SpO_2$, % SpMET, % SpCO, BPM, PI, and PVI), and upper and lower alarm limits that have been set for each parameter. For example, in the embodiment illustrated in FIG. 7, a device has been set to alarm if the patient's % $SpO_2$ level drops below 90, % SpMET exceeds 3.0, % SpCO exceeds 43, or if BPM drops below 50 or exceeds 140.

A history view area 730 (sometimes referred to as the analysis panel 730) in certain implementations can show medical event data corresponding to a selected patient monitor status module 712. This medical event data can be obtained from a journal database for inclusion in the GUI 700. The historical view 730 can show, for example, when a sensor was connected or disconnected from a patient, when alarms were active, and when a patient was admitted to the hospital or department, etc. The history view area 730 can also be configured to show historical trend, waveform, or patient wellness data obtained from an RRDB over a desired time period instead of, or in addition to, the journaled medical event data.

Figure 8:
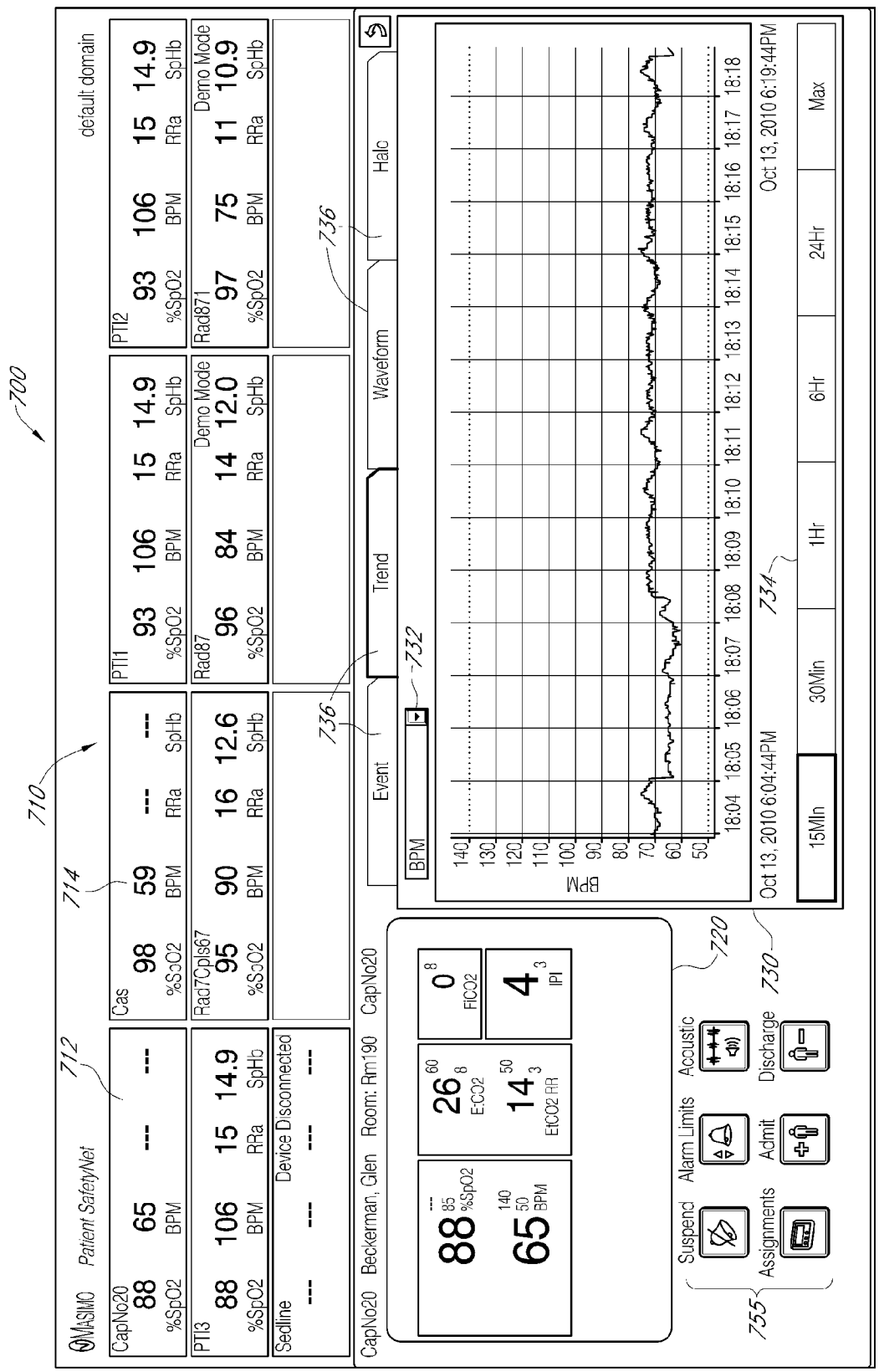

For example, FIG. 8 illustrates another embodiment of the GUI 700 in which the history view area (or analysis panel) 730 is configured to display trend data associated with a selected medical patient over a selected time period. The trend data can be retrieved from a round-robin database, as discussed above. The analysis panel 730 includes a parameter menu 732, which is used to select the particular parameter to be displayed on the analysis panel 730. In FIG. 8, the patient's pulse rate (beats per minute, or BPM) has been selected for display. The parameter menu 732 will generally allow a user to select any one or more of the physiological parameters of a patient that are and/or have been recorded by a multi-patient monitoring system. For example, in one embodiment, the parameter menu 732 allows a user to see historical data of at least any of the physiological parameters shown in the patient monitor view area (or virtual display area) 720.

The user is able to select a time period by activating an appropriate time period selector 734. For example, the time period selector 734 allows the user to view the most recent 15 minutes, 30 minutes, or 1, 6, or 24 hours, or the maximum stored data associated with the selected physiological parameter. In some embodiments, the user is able to select a start time and a duration, or an end time and a duration, or start and end times as the time period. The selected time period is illustrated along the x-axis of the analysis panel 730.

In some embodiments, the analysis panel 730 also displays a markers that correspond to one or more events stored in the patient's database. For example, any of the event discussed above and illustrated in FIG. 7 could be represented as small yellow bars positioned at the corresponding times along the x-axis of the analysis panel 730. In this manner, a clinician can instantly determine whether an event occurred before, after, or at the same time of displayed trend data. For example, a clinician would be able to determine if a sudden drop in a parameter's value might be due to a sensor being disconnected from the patient or the sensor registering a "probe-off" error.

In the embodiment of FIG. 8, the patient status display area (or dashboard) 710 includes patient status modules 712 that display real-time physiological parameters of the medical patients attached to physiological monitors in communication with a multi-patient monitoring system (such as MMS 120, 220). For example, the patient status module 712 associated with the physiological monitor having ID "CapNo20" displays % $SpO_2$ and BPM data only, while the patient status module 712 associated with the physiological monitor having ID "Rad87" provides % $SpO_2$, BPM, RRa (respiratory rate) and SpHb data.

Figure 9:
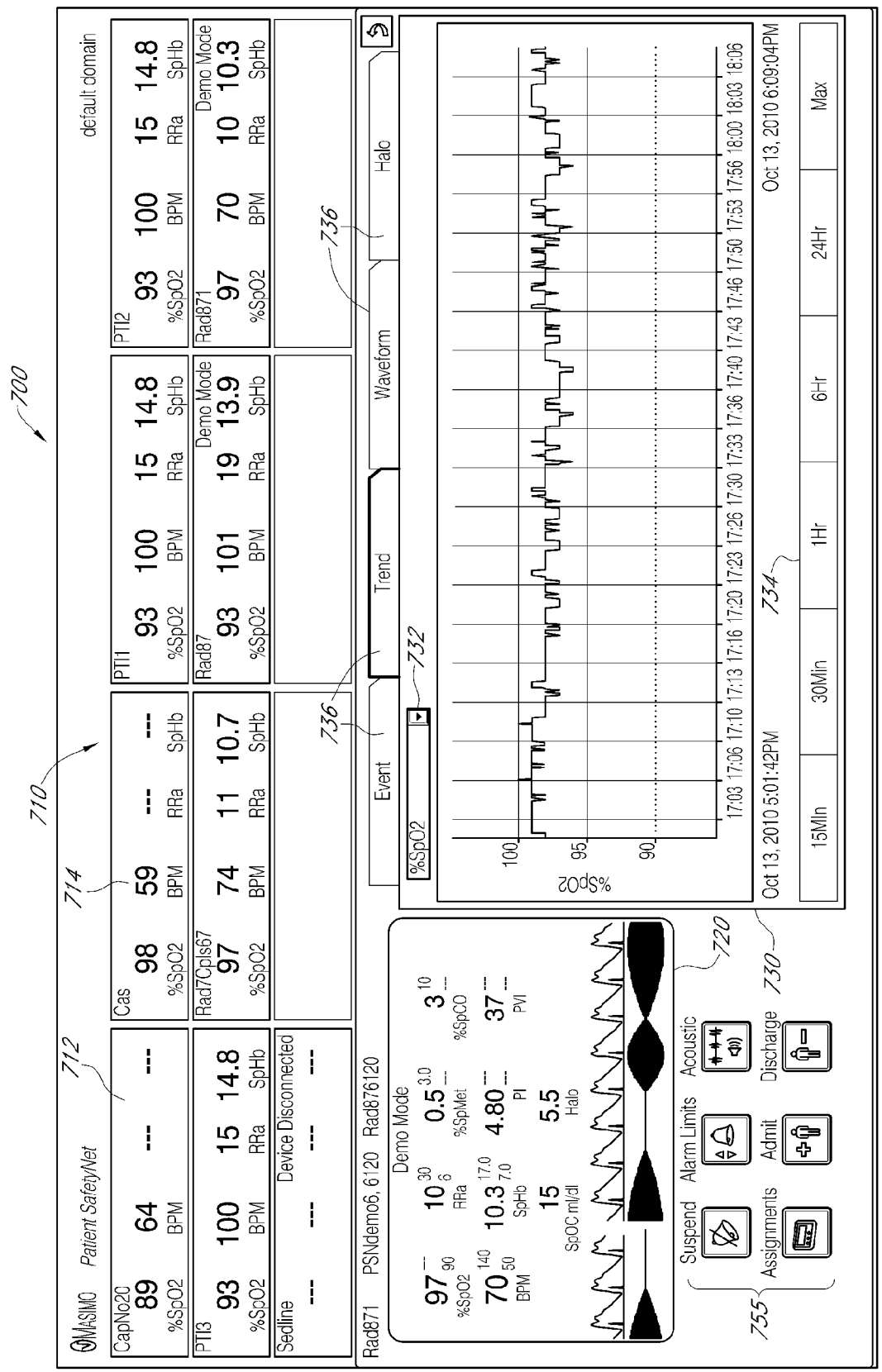

FIG. 9 illustrates another embodiment of the GUI 700 configured to display trend data. However, in the embodiment of FIG. 9, the user has selected % $SpO_2$ data for display in the analysis panel 730. In addition, the patient monitor view area (or virtual display) 720 is configured to display real-time parameter values and real-time waveforms associated with particular parameters. The corresponding parameters and waveforms of the virtual display 720 can be represented in the same color to show which waveform corresponds to which parameter.

The GUI 700 also includes various analysis tabs 736, which allow the user to modify the contents displayed in the analysis panel 730. For example, in one embodiment, the GUI 700 includes "Event," "Trend," "Waveform," and "Halo" analysis tabs. Selecting the "Event" tab causes the analysis panel 730 to display event data, as shown in FIG. 7. Selecting the "Trend" tab causes the analysis panel 730 to display trend data, as shown in FIGS. 8 and 9. Selecting the "Waveform" or "Halo" tabs cause the analysis panel 730 to display waveform and patient wellness information, as illustrated in FIGS. 10 and 11 and discussed below.

Figure 10:
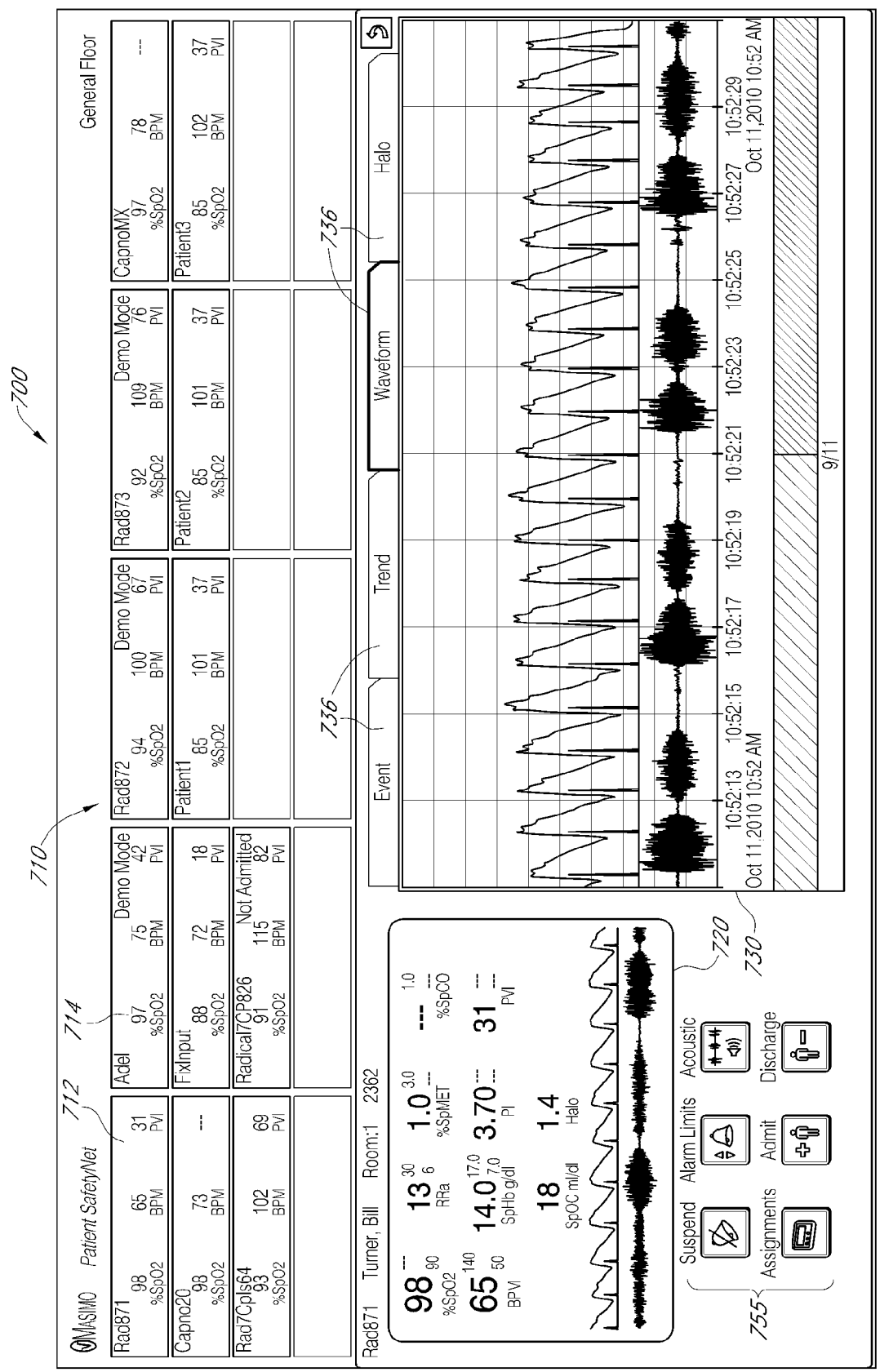

FIG. 10 illustrates a GUI 700 configured to display real-time waveform data within its virtual display 720 and historical waveform data within its analysis panel 730. Similar to the trend data configuration of FIG. 9, the user is able to select a time period of interest by activating a time period selector 734 (not shown) or by selecting a particular start time, end time, and/or duration. The analysis panel 730 can also display event markers (not shown), as discussed above. The real-time waveform data can be received from a physiological monitor while the historical waveform data can be received from a round-robin database, as discussed above.

The analysis panel 730 of FIG. 10 shows waveform data received from one or more physiological monitors coupled to a medical patient. For example, the waveform data includes the waveforms used to determine any one or more of physiological parameters of the medical patient, including but not limited to % $SpO_2$, % SpMET, % SpCO, BPM, RRa, % SpHb, PI, PVI, SpOC, patient wellness (sometimes referred to as Halo), and/or others.

Figure 11:
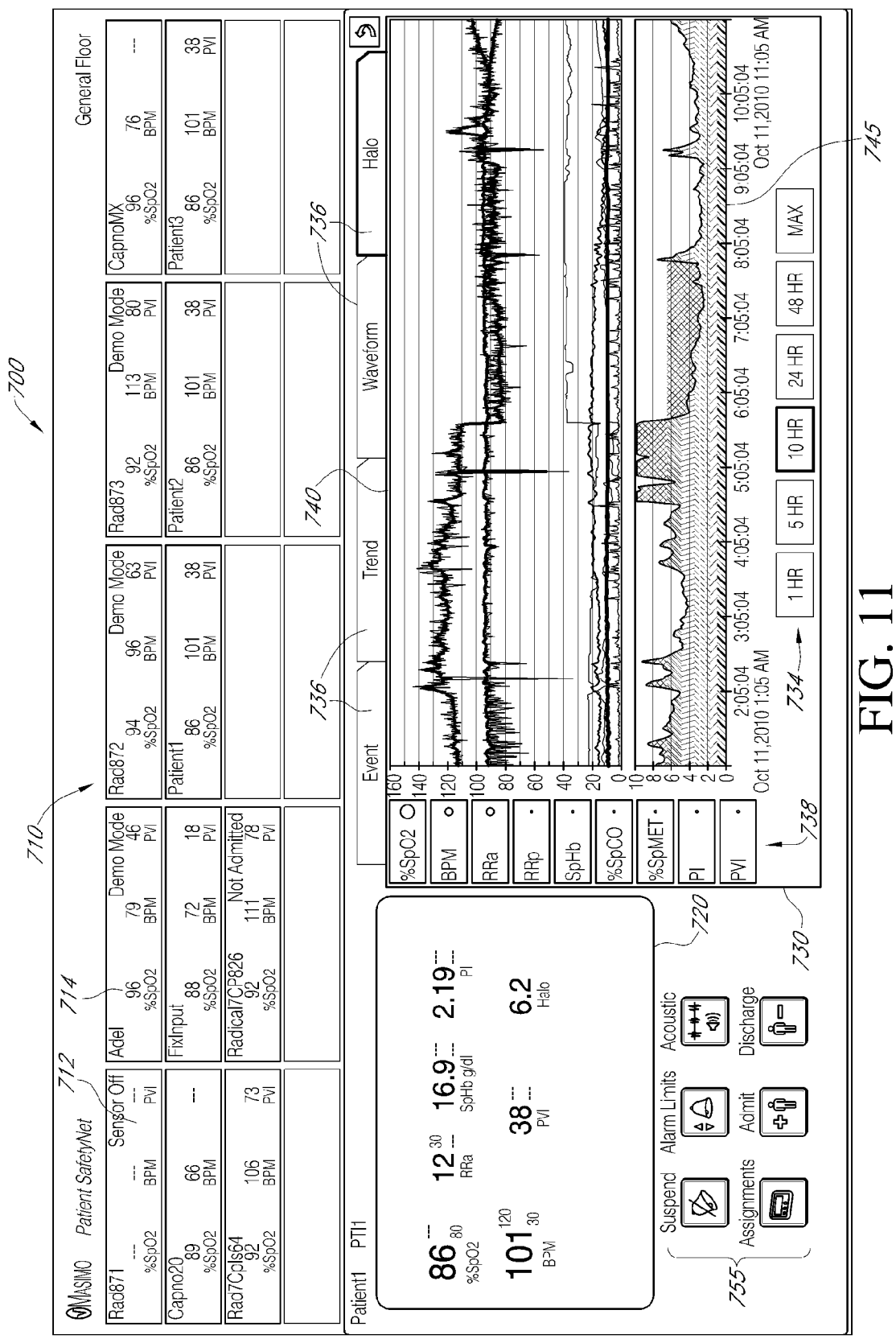

FIG. 11 illustrates a GUI 700 configured to display information relating to a patient's overall health or wellness within its analysis panel 730. Historical waveform information relating to multiple physiological parameters are illustrated in a first, or upper portion 740 of the analysis panel 730. A second, or lower portion 745 of the analysis panel illustrates the overall health or wellness of the medical patient based. Overall health or wellness may be determined based upon the combined effect of each of the monitored physiological parameters. The patient's overall health may be represented as a risk value between 0-10, where 0 is low risk of an adverse event and where 10 is high risk of an adverse event. The lower portion 745 of the analysis panel 730 illustrates the historical risk value of the patient over time. Different colors may be used to graphically illustrate when the risk value exceeds certain threshold levels. For example, the waveform shown in the lower portion 745 may be filled blue for values less than 1, but red for values greater than 7, with different colors for different bands inbetween. Such coloring is illustrated by the different fill patterns within the waveform shown in the lower portion 745 of the analysis panel 730 of FIG. 11.

The analysis panel 730 also includes parameter impact buttons 738 that correspond to the waveforms displayed in the analysis panel's 730 upper portion 740. Deselecting a particular parameter impact button 738 removes the associated waveform from the upper portion 740 and causes the risk waveform shown in the lower portion 745 to be calculated without considering the impact of the deselected parameter. Such functionality is useful to help clinicians determine the impact of a particular parameter on the patient's overall health and/or risk of an adverse event.

In addition, each parameter impact button 738 includes a indicator to show the significance or weight of the parameter's impact on the patient's overall health or risk. In the embodiment of FIG. 11, the indicators are provided as circles within each parameter impact button 738. Larger diameter circles indicate greater impact on the patient's overall health or risk. For example, the illustrated parameter impact buttons 738 indicate that % $SpO_2$ is having the greatest significance or weight in calculating the patient's risk.

Additional information regarding the "Halo Index," overall patient health, wellness and risk of adverse events are described in U.S. Provisional No. 61/391,067, filed Oct. 7, 2010, which is incorporated by reference in its entirety.

The GUI 700 of any of the embodiments discussed above, can also include one or more system controls 755. The system controls 755 can be configured to activate various system-level or device-level functions. For example, in one embodiment, the GUI 700 includes "Suspend," "Alarm Limits," "Acoustic," "Assignments," Admit," and/or "Discharge" system controls 755.

The Suspend control 755 can be selected to suspend or deactivate an alarm. For example, the GUI 700 or the device displaying the GUI 700 may be configured to flash, activate an audible tone, send a page or make a telephone call to a clinician (or other function) if a physiological alarm is activated. The Suspend control 755 can be used to temporarily disable and/or enable such alarming functionality.

The Alarm Limits control 755 may be selected to increase or decrease the threshold level above- or below which an alarm will activate. The Acoustic control 755 may be selected to port an audible output to a listening device. For example, the Acoustic control 755 may be selected to cause the sound of a patient's heart beat or respiration (or other audible physiological function) to a listening device. Listening devices include headphones that can be attached to a port of the device displaying the GUI 700, or a remote listening device, such as a user's telephone, wireless headset (e.g., Bluetooth, etc.), over a network, etc. Additional information regarding the Acoustic control and sending physiological sounds directly, indirectly, over a network, wirelessly, etc., are described in U.S. Provisional Nos. 61/391,098 filed Oct. 8, 2010 filed Oct. 8, 2010, which is incorporated by reference in its entirety.

The Assignments control 755 may be selected to assign the monitored patients to particular nurses within a healthcare facility. For example, in some embodiments, when an alarm is activated, an assigned nurse is informed of the alarm via a page, phone call, or other message. The Assignments control 755 can be used to reassign patients, for example, when a previously-assigned nurse's shift ends (or if the nurse is assigned to a different patient) and a new nurse is assigned.

The Admit and Discharge controls 755 may be selected to associate (or disassociate) the various physiological devices represented in the patient status display area 710 or dashboard, with particular medical patients.

Furthermore, although the embodiments above have been described with respect with various networked configurations, it should be understood that the functionality described herein may be embodied in just a single medical device. For example, in some embodiments, a patient monitor includes a processor or other controller configured to create and/or interact with one or more RRDBs and/or journal databases. For example, the patient monitor itself can include any one or more of a monitoring module, RRDB module, journal module, user interface module, network management module, RRDB and journal database, as described above. Furthermore, in some embodiments, a medical monitor is configured to act as a stand-alone device in a first mode in which the device is not attached to a network. The device generates and records physiological data (including parameters and streams) based upon signals from sensors coupled to the device and a medical patient. The medical monitor is further configured to automatically connect to a medical network (e.g., network 100, 110, 200, 210) and/or to automatically send the data stored in the monitor to a MMS, RRDB, and/or journal database (e.g., MMS 120, 220, RRDB 122, 222, and/or journal database 124, 224 described above, or others) when the medical monitor is within wireless range or physically attached to such a medical network.

Depending on the embodiment, certain acts, events, or functions of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

While the above detailed description has shown, described, and pointed out novel features as applied to various embodiments, it will be understood that various omissions, substitutions, and changes in the form and details of the device or process illustrated may be made without departing from the spirit of the disclosure. As will be recognized, certain embodiments of the inventions described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope.

What is claimed is:

1. A method of automatically adjusting alarm levels for patient monitoring devices, the method comprising:
by one or more processors:
obtaining alarm response data regarding clinician response times to alarms from one or more patient monitors, the clinician response times being based on times at which one or more clinicians respond to the alarms;
storing the alarm response data regarding the clinician response times to the alarms in a journal database;
analyzing the alarm response data to determine whether a selected one of the clinician response times by a first clinician to a first one of the alarms output by a first one of the patient monitors exceeds a threshold;
in response to determining that the selected clinician response time exceeds the threshold, automatically adjusting an alarm setting of the first patient monitor for second alarms subsequent to the first alarm;
determining how many of the alarms were set outside of physiologic norms and storing data regarding the number of alarms set outside of the physiologic norms in the journal database; and
using the alarm response data to identify healthcare practitioners who need additional training,
wherein said automatically adjusting the alarm setting comprises raising or lowering the threshold of the second alarms output by the first patient monitor, and
wherein the alarm response data comprises data regarding one or more of the following: how long it took for a particular healthcare practitioner to respond to the alarms, how long it took a particular shift of healthcare practitioners to respond to the alarms, or how long it took a particular unit of healthcare practitioners to respond to the alarms.

2. The method of claim 1, wherein said automatically adjusting the alarm setting comprises increasing a volume of the second alarms output by the first patient monitor.

3. The method of claim 1, wherein said automatically adjusting the alarm setting comprises changing a tone of the second alarms output by the first patient monitor.

4. A system for automatically adjusting alarm levels for patient monitoring devices, the system comprising:
a multi-patient monitoring system comprising one or more processors, the multi-patient monitoring system configured to:
obtain alarm response data regarding clinician response times to alarms from one or more patient monitors, the clinician response times based on one or more times at which one or more clinicians responded to the alarms;
store the alarm response data regarding the clinician response times to the alarms in a journal database;
analyze the alarm response data to determine whether a selected one of the clinician response times by a first clinician to a first one of the alarms output by a first one of the patient monitors exceeds a threshold;
in response to a determination that the selected clinician response time exceeds the threshold, automatically adjust an alarm setting of the first patient monitor for second alarms subsequent to the first alarm
determine how many of the alarms were set outside of physiologic norms and store data regarding the number of alarms set outside of the physiologic norms in the journal database; and
use the alarm response data to identify healthcare practitioners who need additional training,
wherein said automatically adjusting of the alarm setting comprises at least raising or lowering the threshold level of the second alarms output by the first patient monitor, and
wherein the alarm response data comprises data regarding one or more of the following: how long it took for a particular healthcare practitioner to respond to the alarms, how long it took a particular shift of healthcare practitioners to respond to the alarms, or how long it took a particular unit of healthcare practitioners to respond to the alarms.

5. The system of claim 4, wherein the multi-patient monitoring system is further configured to perform said automatic adjustment of the alarm setting by at least increasing a volume of the second alarms output by the first patient monitor.

6. The system of claim 4, wherein the multi-patient monitoring system is further configured to perform said automatic adjustment of the alarm setting by at least changing a tone of the second alarms output by the first patient monitor.

7. Non-transitory physical computer storage comprising instructions stored thereon that, when executed in one or more processors, are configured to implement a method of automatically adjusting alarm levels for patient monitoring devices, the method comprising:

obtaining alarm response data regarding clinician response times to alarms from one or more patient monitors, the clinician response times being based on times at which one or more clinicians respond to the alarms;

storing the alarm response data regarding the clinician response times to the alarms in a journal database;

analyzing the alarm response data to determine whether a selected one of the clinician response times by a first clinician to a first one of the alarms output by a first one of the patient monitors exceeds a threshold; and in response to determining that the selected clinician response time exceeds the threshold, automatically adjusting an alarm setting of the first patient monitor for second alarms subsequent to the first alarm determining how many of the alarms were set outside of physiologic norms and storing data regarding the number of alarms set outside of the physiologic norms in the alarm response data; and using the alarm response data to identify healthcare practitioners who need additional training, wherein said automatically adjusting the alarm setting comprises raising or lowering the threshold of the second alarms output by the first patient monitor, and wherein the alarm response data comprises data regarding one or more of the following: how long it took for a particular healthcare practitioner to respond to the alarms, how long it took a particular shift of healthcare practitioners to respond to the alarms, or how long it took a particular unit of healthcare practitioners to respond to the alarms.

* * * * *